United States Patent
Guire et al.

(10) Patent No.: US 11,407,977 B2
(45) Date of Patent: Aug. 9, 2022

(54) TISSUE SCAFFOLDS FOR ELECTRICALLY EXCITABLE CELLS

(71) Applicant: Innovative Surface Technologies, Inc., St. Paul, MN (US)

(72) Inventors: Eric Guire, St. Paul, MN (US); Christopher Bahr, Coon Rapids, MN (US)

(73) Assignee: INNOVATIVE SURFACE TECHNOLOGIES, INC., St. Paul, MN (US)

( * ) Notice: Subject to any disclaimer, the term of this patent is extended or adjusted under 35 U.S.C. 154(b) by 73 days.

(21) Appl. No.: 16/684,560

(22) Filed: Nov. 14, 2019

(65) Prior Publication Data

US 2020/0095570 A1    Mar. 26, 2020

Related U.S. Application Data

(63) Continuation of application No. 15/028,709, filed as application No. PCT/US2014/060197 on Oct. 11, 2014, now abandoned.

(60) Provisional application No. 61/890,193, filed on Oct. 12, 2013.

(51) Int. Cl.
| | | |
|---|---|---|
| C12N 5/00 | (2006.01) | |
| C12M 1/12 | (2006.01) | |
| C12N 11/089 | (2020.01) | |
| C12N 11/096 | (2020.01) | |
| C12M 1/34 | (2006.01) | |

(52) U.S. Cl.
CPC ........... *C12N 5/0068* (2013.01); *C12M 25/14* (2013.01); *C12M 41/46* (2013.01); *C12N 11/089* (2020.01); *C12N 11/096* (2020.01); *C12N 2533/30* (2013.01)

(58) Field of Classification Search
CPC .. C12N 11/08; C12N 5/0068; C12N 2533/30; C12M 41/46; C12M 25/14
See application file for complete search history.

(56) References Cited

U.S. PATENT DOCUMENTS

| | | | |
|---|---|---|---|
| 4,973,493 | A | 11/1990 | Guire |
| 5,002,582 | A | 3/1991 | Guire et al. |
| 5,258,041 | A | 11/1993 | Guire et al. |
| 5,563,056 | A | 10/1996 | Swan et al. |
| 5,637,460 | A | 6/1997 | Swan et al. |
| 5,834,029 | A | 11/1998 | Bellamkonda et al. |
| 5,898,000 | A | 4/1999 | Matsuda et al. |
| 6,278,018 | B1 | 8/2001 | Swan |
| 7,772,393 | B2 | 8/2010 | Guire et al. |
| 7,807,750 | B2 | 10/2010 | Taton et al. |
| 7,943,234 | B2 | 5/2011 | Lawin et al. |
| 7,989,619 | B2 | 8/2011 | Guire et al. |
| 8,367,410 | B2 | 2/2013 | Radisic et al. |
| 8,487,137 | B2 | 7/2013 | Guire et al. |
| 8,496,857 | B2 | 7/2013 | Guire et al. |
| 8,691,543 | B2 | 4/2014 | Gaudette et al. |
| 8,709,809 | B2 | 4/2014 | Wen et al. |
| 8,771,582 | B2 | 7/2014 | Phaneuf et al. |
| 8,779,206 | B2 | 7/2014 | Guire et al. |
| 2003/0054333 | A1 | 3/2003 | Hickman et al. |
| 2004/0009537 | A1 | 1/2004 | Roos et al. |
| 2005/0003530 | A1 | 1/2005 | Gerlach |
| 2008/0220042 | A1 | 9/2008 | Hashi et al. |
| 2010/0120115 | A1 | 5/2010 | Ogle et al. |
| 2010/0233115 | A1 | 9/2010 | Patel et al. |
| 2010/0255581 | A1 | 10/2010 | Naqvi et al. |
| 2010/0273258 | A1 | 10/2010 | Lannutti et al. |
| 2011/0293685 | A1 | 12/2011 | Kuo et al. |
| 2012/0122728 | A1 | 5/2012 | Hickman et al. |
| 2013/0143230 | A1 | 6/2013 | Tolias et al. |
| 2013/0197663 | A1 | 8/2013 | MacEwan et al. |
| 2014/0011938 | A1 | 1/2014 | Guire et al. |
| 2014/0294783 | A1 | 10/2014 | Wen et al. |
| 2014/0315235 | A1 | 10/2014 | Puschmann et al. |

FOREIGN PATENT DOCUMENTS

WO    2011159889 A2    12/2011

OTHER PUBLICATIONS

Lee, SJ et al. The use of thermal treatments to enhance the mechanical properties of electrospun poly(e-caprolactone) scaffolds. Biomaterials. 2008. 29: 1422-1430. (Year: 2008).*
International Search Report for corresponding PCT/US14/60197 (3 pages).
Secasanu et al., A novel electrospinning target to improve the yield of uniaxially aligned fibers, Biotechnol. Prog. 25(4):1169-1175 (2009).
Yla-Outinen, Laura, Functionality of Human Stem Cell Derived Neuronal Networks Biomimetic environment and characterization, Univ. of Tampere, academic dissertation, 146pp (2012).

(Continued)

*Primary Examiner* — Renee Claytor
*Assistant Examiner* — Susan E. Fernandez
(74) *Attorney, Agent, or Firm* — Weaver Legal and Consulting LLC; Karrie Gemignani Weaver

(57) ABSTRACT

Inventive concepts relate generally to nanofibrous scaffolds useful for electrophysiological assays. Scaffolds include polymeric nanofibrous components and electrically excitable cells immobilized at a distinct cell seeding domains on the scaffold. Methods and kits including the scaffolds are also described.

19 Claims, 8 Drawing Sheets

(56) References Cited

OTHER PUBLICATIONS

Natarajan, Anupama, Patterned cell cultures for high throughput studies of cell electrophysiology and drug screening applications, Univ. Cent. Florida, dissertation 111pp (2010).
Li et al., Tissue-Engineered Platforms of Axon Guidance, Tissue Engineering Part B 14(1): 33-51 (2008).
Johnston, D. et al., Foundations of Cellular Neurophysiology, Massachusetts Institute of Technology, pp. 428-430 (1995).

* cited by examiner

TISSUE SCAFFOLDS FOR ELECTRICALLY EXCITABLE CELLS

CROSS REFERENCE TO RELATED APPLICATIONS

This application claims benefit under 35 U.S.C. § 119(e) to U.S. Patent Application Ser. No. 61/890,193, entitled "CELL GROWTH SUBSTRATES CONTAINING OPEN FIELD ARCHITECTURES," filed Oct. 12, 2013, the contents of which are incorporated herein in their entirety for all purposes.

This invention was made with government support under Grant No. 1R43MH101958-01, awarded by the National Institute of Mental Health. The government has certain rights in the invention.

FIELD OF THE INVENTION

Inventive concepts relate generally to the field of drug discovery and drug development for the screening of disease treatment.

BACKGROUND

The global drug discovery technologies market is projected to reach $19.9 Billion by 2017. In the primary methodology, High Throughput drug Screening process (HTS), massive libraries of chemical entities are evaluated for activity towards a target of interest, often expressed in a suitable cell line.

This identification process is then followed by hit confirmation, hit expansion, and lead optimization for drug candidates. Additionally, high-content screening utilizing fluorescence, morphological, electrophysiological, or other parameters can be employed in the search for molecules that can provide the desirable phenotypic alteration to a cells. Some important shortcomings of in vitro cellular assays for HTS have historically been unnatural expression levels of target genes, abnormal posttranslational modification or subcellular trafficking of targets, physiologically irrelevant signal transduction events, and/or missing or incorrect target cofactors such as allosteric modulators. Furthermore, for electrically excitable cells such as neurons, circuit-level electrophysiological activity of organized tissues which may normally regulate drug targets in vivo, is absent in vitro. Therefore, it is desirable to perform a secondary screening process to validate confirmed hits.

The secondary screening process provides information that is more in vivo-like, whereby the natural function of the target is evaluated under more relevant physiological conditions. For this purpose, the use of live mammalian tissues or highly engineered bioartificial tissues can significantly enhance the drug screening process. Indeed, the development of artificial human tissues (such as human tissue chips) for use earlier in the drug screening process is expected to produce significant cost savings through the elimination of drugs with potential for serious adverse effects sooner in the drug development process. This development can result in safer and more effective drugs, speed up their time to market, and reduce the number of animals used in their development.

Acute brain slices have provided the basis for much of our understanding of mammalian neurophysiology. Accordingly, they are an important tool in the drug screening process for functional evaluation of targets within the CNS and spinal cord, as well as for the identification of potential off-target effects. Acute, or "ex vivo," brain slices are currently used in part due to their superior physiological relevance compared to dissociated neuronal cultures, but also due to the relative ease of their experimental manipulation as compared to work performed in whole animals. The use of acute brain slices (typically rat or mouse) in drug screening has grown over the past decade due to the adoption of planar multi-electrode array (MEA) technology, whereby extracellular electrophysiological recording techniques with higher throughput can be achieved. However, the low number of brain slices that can be produced per animal, coupled with the high costs of animal care and their labor-intensive use, is a significant drawback to this approach. Moreover, due to interspecies genetic variation, preclinical data acquired through the use of rodent brain slices will be of limited predictive power for human clinical trials and postmarket surveillance.

The ideal drug screening assay would be relatively inexpensive, high-throughput, and measure the responses of human cells or tissues to drugs in an in vivo-like context. Unfortunately, HTS most often examines the effect of drugs on single cells grown in a context that largely lacks in vivo-like characteristics such as nanotopography and cell-cell contacts with various cell types found in native tissues. This increases the chance for mischaracterization of a drug's effects including the misidentification or non-identification of likely off-target effects.

SUMMARY OF INVENTION

Inventive concepts relate generally to scaffolds for electrophysiological assays that are composed of nanofibrous materials and include specific architecture and surface chemistry to mimic native tissue environments. Inventive devices and methods can provide a functional electrophysiological circuit that includes synapses, thereby providing a powerful tool for drug screening.

In some implementations, there are provided nanofibrous scaffolds comprising: (a) a layer of unaligned polymeric nanofibers; (b) a first population of electrically excitable cells immobilized at a first cell seeding domain on the scaffold; (c) a second population of electrically excitable cells immobilized at a second cell seeding domain on the scaffold at a site that is distinct from the first cell seeding domain; and (d) at least first and second aligned nanofibrous conduits provided on a surface of the unaligned nanofibers, wherein the first conduit is in contact with the first cell seeding domain, and the second conduit is in contact with the second cell seeding domain, and wherein the first conduit and second conduit contact each other at an intersection, The unaligned polymeric nanofibers can be randomly oriented.

In some aspects, the electrically excitable cells of the first cell seeding domain are neural cells, and the electrically excitable cells of the second cell seeding domain are selected from neural cells and muscle cells. The neural cells can be neurons. Optionally, the scaffold can further comprise glia or other support cells. In some implementations, the electrically excitable cells are derived from human cells. The electrically excitable cells can be neural or glial progenitor cells, neural or glial precursor cells, neurotypic cells, pluripotent cells, stem cells, cells which can be differentiated into electrically excitable cells in situ, cells rendered electrically excitable by gene transfection or viral transduction, or any combination of these. The electrically excitable cells can be primary cells.

In some implementations, the electrically excitable cells form synapses at the intersection of the first and second conduit. In some aspects, the axons of one cell population can synapse with a second cell population on their soma (for example, as occurs with cells lacking dendrites).

Optionally, the scaffold can include at least one electrode operably coupled thereto.

In some implementations, the scaffold can further comprise a support selected from petri dishes, flasks, multiwell plates, slides, films, frames, and hydrogels. The support can include electrical components such as circuits and electrical connectors. The support can be fabricated from any of a large variety of non-cytotoxic solids and gels. Illustrative support material includes, but is not limited to, silicones, polyolefins, vinyl polymers, polystyrenes, polyacrylates, poly methacrylates, polyacrylonitriles, poly(vinylacetates), poly(vinyl alcohols), chlorine-containing polymers such as polyvinyl) chloride, polyoxymethylenes, polycarbonates, polyamides, polyimides, polyurethanes, phenolics, amino-epoxy resins, polyesters, polyethers, cellulose-based plastics, rubber-like plastics, copolymers, ceramics, metals, silicates, or any mixtures or combinations thereof. Other suitable support materials include silica glass, alginate, collagen, various hydrogels, self-assembled nanofibers, proteins, nucleic acids, polysaccharides, drawn or spun nanofibers, synthetic extracellular matrix, animal and plant extracts, and the like.

The nanofibers of the scaffold can be electrospun nanofibers. Optionally, the nanofibers comprise at least one chemically reactive functional group or latent reactive group. Illustrative latent reactive groups include, but are not limited to, anthraquinone, aryl azide, aryl ketone, aryl ketone derivative, halophenyl azide, diazerine, or any mixtures or combinations of any of these. Illustrative chemically reactive groups include, but are not limited to, "click" groups (chemically reactive groups commonly used in "click chemistry") or amine groups.

In some implementations, the scaffold can further comprise one or more cell culture agents or gradients of cell culture agents on one or more portions of the scaffold. The one or more cell culture agents can be selected from cell attachment, growth, proliferation, or differentiation agents, or a combination of any two or more of these.

In some aspects, the scaffold can include a microscale or a nanoscale topography that modulates cell growth or proliferation. Optionally, the scaffold can comprise a passivating polymer on a surface of the scaffold. Passivating regions of the scaffold may also be generated using superhydrophobic compositions, such as those described in commonly owned U.S. Pat. No. 7,943,234 (Lawin et al., issued May 17, 2011). Optionally, one or more agents can be provided on the aligned conduits to modulate the growth of neurites, axons, dendrites, or their support cells.

Optionally, the scaffold can further include an electrically conductive material. In some implementations, the scaffold comprises a plurality of porous sheets or films assembled in a laminar configuration.

In additional implementations, inventive concepts provide methods of producing a nanofibrous scaffold composite comprising steps of: (a) providing a nanofibrous scaffold; (b) providing a cell culture agent at two or more distinct domains on a surface of the scaffold, thereby forming two or more distinct cell seeding domains; (c) disposing two or more aligned nanofibrous conduits on the scaffold surface, in a configuration so that each conduit is in contact with one cell seeding domain, and each conduit intersects the other conduit at an intersection located separate from the cell seeding domains; and (d) culturing electrically excitable cells on the distinct cell seeding domains under conditions to form functional chemical synapses between the electrically excitable cells. Such synapses may form at the intersection of nanofibrous conduits, or at a location along one or more nanofiber conduits. Optionally, a passivating polymer can be provided to an area of the scaffold outside the cell seeding domains by applying the passivating polymer to the surface in combination with photolithographic masks or by printing. In further aspects, nanofibers making up the area outside the cell seeding domains can themselves be fabricated of a passivating polymer.

Photopatterning may be used to influence the architecture or spatial arrangement of cells and cell processes on the growth substrate. Optionally, multiple layers of nanofiber mats may be annealed. Further immobilized growth factors are suitable for enhancing cell differentiation into functional circuits of electrically excitable cells on the scaffolds, for example when culturing stem cells or neural precursor cells. Multiple circuits may be generated to model various neural pathways that may include glutamatergic, serotonergic, GABAergic, histaminergic, peptidergic, noradrenergic, glycinergic, opioid, dopaminergic, and/or cholinergic transmitter phenotypes, etc.

In some implementations, the step of providing a cell culture agent at two or more domains on a surface of the scaffold can comprise providing one or more growth factors, extracellular matrix components, or cell attachment polymers.

In further aspects, devices are provided for electrophysiological screening, the devices comprising: (a) a nanofibrous scaffold; (b) at least first and second cell seeding domains; and (c) at least first and second nanofibrous conduits arranged on the scaffold, wherein the first conduit is in contact with the first cell seeding domain, and the second conduit is in contact with the second cell seeding domain, wherein the first conduit and the second conduit contact each other at an intersection, and wherein the first and second cell seeding domains, and the first and second nanofibrous conduits do not contact each other outside the intersection.

In some implementations, cell growth substrates are described comprising: (a) a support surface for cellular attachment; (b) an open field architecture; wherein an open field potential is generated by a group of electrically excitable cells having been cultured on the substrate; wherein the generation of an open field potential is enabled by a spatial arrangement of electrically excitable cells, neurites, axons, or dendrites contained in the group of cells; and wherein the arrangement is provided by the open field architecture of the growth substrate. In some aspects, the scaffold can comprise a plurality of porous sheets or films assembled in a laminar configuration.

In some aspects, inventive concepts provide enhanced ability to observe, measure and record the ensemble activity of electrically active cells in vitro. By providing a bioartificial scaffold that directs cell growth in a manner that mimics the cells' native environment, inventive devices can overcome limitations of prior methodologies that require either whole living organisms or organs (such as whole brain, heart or other muscle), excised tissue, and/or dissociated cells from excised tissue.

In some aspects, inventive concepts have found ways to mimic the natural environment where excitable cells exist within a closed system. For example, inventive concepts have found a way to mimic the natural brain environment where neural cells exist naturally. In some implementations, inventive concepts provide a bioartificial brain slice scaffold for use in electrophysiological assays. The scaffold can serve as a platform for the generation of human and non-human bioartificial brain slices compatible with multi-electrode arrays used for high throughput and high content drug screening of CNS and spinal cord targets, as well as other electrophysiological stimulation or recording techniques. Because the bioartificial brain slices can be continuously generated from a cell culture, they can reduce or eliminate use of animals to generate ex vivo brain slices. Thus, in some aspects, inventive scaffolds can greatly facilitate automation, throughput, and cost savings relating to the drug screening process.

Growth substrates and scaffolds that produce cells and tissues with high physiological relevance or more in vivo like characteristics can enhance drug screening—putting safer medicines on the market in less time and at lower cost—by more accurately predicting clinical outcomes. Hence, the convenience, cost savings and throughput of existing extracellular brain slice recording techniques on planar multielectrode arrays (MEAs) can be further unlocked through the use of this inventive technology. The predictive power of this technology for human clinical trials will be significantly enhanced through the use of human cells grown in an in vivo like context.

In one embodiment, inventive approaches combine the use of photoreactive nanofibers, control over nanoscale topography, and photopatterning to generate scaffolds of similar size and overall architecture to native hippocampal brain slices derived from rats. The combination of these attributes can enable the scaffold to direct the development of nascent bioartificial brain tissue into laminar circuits up to 100, up to 200, up to 300, up to 400, up to 500 microns thick that can be used for the generation of open field potentials. The size and architecture is chosen to mimic the CA1-Schaffer collateral pathway of the rat hippocampal brain slice preparation because this is the most robust and commonly used preparation for extracellular field recordings. The Schaffer collateral is located between the CA3 region and CA1 region in the hippocampus. Schaffer collaterals are the axons of pyramidal cells that connect two neurons (CA3 and CA1) and transfer information from CA3 to CA1.

In some implementations, inventive scaffolds can be provided that have a thickness in the range of about 10 microns to about 500 microns, or about 25 microns to about 500 microns, or about 50 microns to about 500 microns, or about 100 microns to about 450 microns, or about 100 microns to about 400 microns, or about 200 microns to about 350 microns, or about 250 microns to about 350 microns.

In some aspects, inventive methods and articles can provide one or more advantages, such as an in vivo-like electrophysiology, superior predictive power, lower cost and higher throughput than acute slices, more reproducible results than acute slices, reproduction of circuits that are difficult to harvest from animals due to topology (e.g. VTA-cortex), long-term survival of bioartifical brain slices (weeks rather than hours), ease of genetic manipulation/reporter constructs, simultaneous population and single cell analyses, and reduction of animal use in research.

BRIEF DESCRIPTION OF THE DRAWINGS

FIG. 1A illustrates an idealized open field dipole structure; FIG. 1B illustrates neuronal co-cultures on scaffold with aligned axons and dendrites.

FIG. 2A illustrates nonwoven mat nanofiber scaffolds; FIGS. 2B and 2C show mats including parallel nanofibers; FIG. 2D shows stacking of nanofiber mats in alternating layers. The stacks are then cut and annealed at the edges using a heated die (FIG. 2E).

FIG. 7D shows an SEM image of an illustrative nanofiber mat with photoimmobilized PDL surface (scale bar 250 microns); FIG. 7E shows hippocampal cultures growing on an illustrative nanofibrous surface (scale bar 50 microns). FIGS. 7F and 7G are fluorescent photomicrographs of hippocampal cultures growing on photopatterned PDL areas surrounded by PEG. Live cells were stained with calcein (7F, green fluorescence) and dead cells with ethidium (7G, red fluorescence) (100× magnification).

FIGS. 9d-g show SEM images of processed nanofiber cylinders (d, scale bar 200 microns), (e, scale bar 50 microns), and nanofiber cylinders populated with hippocampal cultures (f, scale bar 100 microns), (g, scale bar 50 microns).

DETAILED DESCRIPTION

Figure 1:
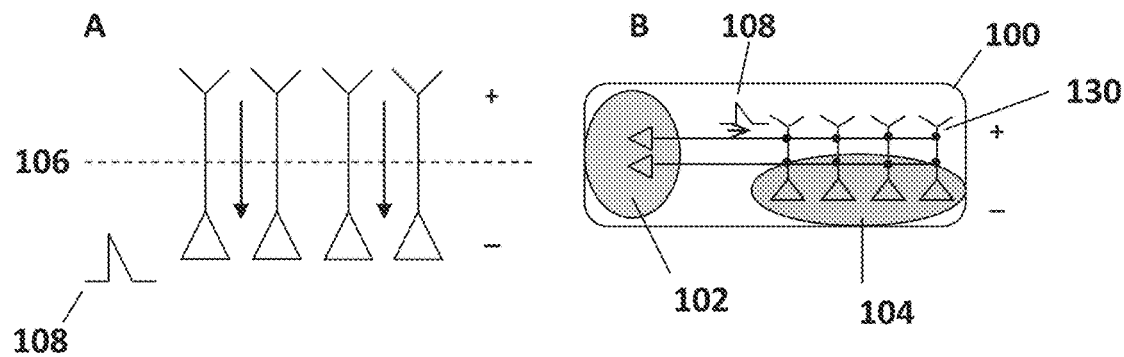
FIG. 1 is a schematic diagram of an illustrative scaffold in accordance with inventive concepts.

The embodiments of the present invention described herein are not intended to be exhaustive or to limit the invention to the precise forms disclosed. Rather, the embodiments are chosen and described so that others skilled in the art can appreciate and understand the principles and practices of inventive concepts. This application is intended to cover adaptations or variations of the present subject matter.

All publications and patents mentioned herein are hereby incorporated by reference to the same extent as if each individual publication or patent application was specifically and individually indicated by reference. The publications and patents disclosed herein are provided solely for their disclosure. Nothing herein is to be construed as an admission that any publication and/or patent is prior art.

In the specification and in the claims, the terms "including" and "comprising" are open-ended terms and should be interpreted to mean "including, but not limited to . . . ." These terms are broader than, and therefore encompass, the more restrictive terms "consisting essentially of" and "consisting of."

As used herein and in the appended claims, the singular forms "a," "an," and "the" include plural reference unless the context clearly dictates otherwise. As such, the terms "a" (or "an"), "one or more" and "at least one" can be used interchangeably herein.

Generally speaking, inventive concepts provide systems for generation and maintenance of functional cells/tissues comprising a composite of electrospun polymer nanofibers provided in a multilayer format within a culture device. A layer can include a single continuous polymer fiber or a plurality of continuous polymer fibers. In various aspects, one or more layers can include unaligned or randomly oriented fibers, or fibers that are aligned and offset from the average axis of alignment of another layer. In various aspects, scaffolds can include a plurality of layers including, without limitation, two, three, four, five, six, or more layers. A "layer" need not cover the entire surface area of another layer of the scaffold. Put another way, each layer can include its own dimensions, including planar surface area and thickness.

Inventive articles and methods can be useful for investigation of multi-cellular interactions. In certain aspects, inventive concepts provide improved compositions and methods for maintenance of excitable cells, or electrically active cells (cells in which an electrical membrane potential changes, creating electrical or electrochemical activity that can be monitored with an electrode). Thus, in some implementations, inventive articles, methods and systems can be useful in the field of electrophysiology. One illustrative embodiment that has particular use in electrophysiology provides a bioartificial brain slice scaffold for patterning 3-dimensional, highly laminar open field arrays of human neuronal co-cultures.

"Electrophysiological" refers to the branch of physiology that deals with the electrical phenomena associated with nervous and other bodily activity. Electrophysiology may include methods to electrically, mechanically, or chemically excite electrically excitable cells, in combination with electrical or non-electrical monitoring techniques such as for example, patch clamping, extracellular field potential recording, optical readouts such as voltage sensitive dyes and calcium indicators, monitoring of cell morphologies, gene expression, signal transduction, and the like.

Electrophysiology is the study of the electrical properties of biological cells and tissues. It involves measurements of voltage change or electric current on a wide variety of scales from single ion channel proteins to whole organs like the heart. In neuroscience, electrophysiology includes measurements of the electrical activity of neurons, and particularly action potential, presynaptic or postsynaptic potential, or field potential activity. Changes in electrical activity in the brain, for example, are generated by changes in the polarization of nerve cells, creating extracellular electrical fields, which are referred to as field potentials. These field potentials are produced primarily by synaptic events. When a neuron is activated by synaptic input, ions flow across the activated area of the membrane. Some patterns of cell membrane activation produce only local currents or "closed" electrical fields, and therefore are unable to generate potential fields that can be measured from a distance. In contrast, an "open" field potential is generated when currents flow beyond the limits of the active cells and their processes. Whether a field potential is open or closed depends upon the geometric arrangement of populations of electrically excitable cells.

As used herein, an "open field potential" is an extracellular electric field potential generated by a group of electrically excitable cells when geometrically arranged in a laminar array, such that a group of electrically excitable processes of the cells in the array are activated nearly simultaneously and a plurality of which are facing in the same direction away from the cell body layer. In this configuration, when there is near-simultaneous activation of dendrites, for example, a strong dipole is produced. In circumstances where the dendrites are activated more radially, and in tissues where the cell bodies layers are not well organized, the potential difference between dendrites and the somas tend to cancel diametrically or otherwise be very small. This is a closed, in contrast to open, field. When open field potentials are elicited by presynaptic stimulation of neurons, changes in the local field potential can be used to monitor synaptic communication between neurons.

Nature generates open field architecture through a complex interplay of genetic programming and environmental cues during tissue development, as well as likely undiscovered mechanisms. Inventive concepts demonstrate that humans can artificially generate a scaffold that causes electrically excitable cells, such as neurons, to form circuits that generate open field potentials. In some implementations, inventive scaffolds include immobilized electrically excitable cells that are cultured in two or more distinct domains, as well as naturalistic synaptic circuitry that permits the distinct cultures to generate open field potentials.

FIG. 1 is a schematic representation of a scaffold for generation of field potentials that is modeled after hippocampal area CA1. FIG. 1A shows an idealized open field dipole structure, wherein the dashed line 106 represents a zero potential line, arrows show flow of current, and the triangular waveform 108 shows depolarization. FIG. 1B illustrates one implementation of inventive concepts, wherein neuronal co-cultures are provided on a functionalized scaffold 100 with perpendicular aligned axons and dendrites. A first cell population of presynaptic cells is provided at a first cell seeding domain 102, and a second cell population of postsynaptic cells is provided at a second cell seeding domain 104. Again, flow of current is represented by the arrows, and depolarization is represented by the triangular waveform 108. Architecture for generation of open field potentials is contained within the scaffold 100. As illustrated in FIG. 1, the first cell seeding domain and second cell seeding domain are positioned at distinct, separate locations on the scaffold 100. In this way, an open field can be generated.

In turn, the phrase "open field architecture" refers to a spatial arrangement of electrically excitable cells and their electrically excitable processes that will generate an open field potential when appropriately stimulated. As used herein, the term "architecture" refers to a 2- or 3-dimensional pattern which directs the attachment of cells, or the growth, differentiation, or morphology of cells, such that the cells form a group, collection, or tissue exhibiting a similar 2- or 3-dimensional pattern after being cultured on a substrate or scaffold containing said architecture.

Inventive articles and methods mimic the natural tissue environment of electrically excitable cells, thereby providing a more accurate model for assessment of potential treatment options. As noted herein, hippocampal CA-1 pyramidal neurons in brain slices provide an ideal model system for studying drug effects on synaptic transmission. Intact synaptic pathways and interneuron circuits can be preserved in thin slices (0.3 to 0.5 mm) of brain tissue which remain viable and physiologically stable. However, as noted herein, use of brain tissue is disadvantageous, Illustrative excitable cells include, but are not limited to, neurons, muscle cells, endocrine cells (e.g., pancreas), and some plant cells. While inventive concepts will be described with reference to neural cells, it will be understood that these concepts can be utilized in connection with other cell types that exhibit electrical properties, such as muscle cells, ocular cells, auditory cells, and the like.

In some implementations, the electrically excitable cells of the first cell seeding domain are neural cells, and the electrically excitable cells of the second cell seeding domain are selected from neural cells and muscle cells. The neural cells can be neurons. Optionally, the scaffold can further comprise glia. The electrically excitable cells can be derived from human cells. In some aspects, the electrically excitable cells are neural or glial progenitor cells, neural or glial precursor cells, neurotypic cells, pluripotent cells (including induced pluripotent, iPS), stem cells, cells which can be differentiated into electrically excitable cells in situ, cells rendered electrically excitable by gene transfection or viral transduction, or any combination of these. The electrically excitable cells can be primary cells.

In one implementation, inventive concepts provide a nanofibrous scaffold comprising: (a) a layer of unaligned polymeric nanofibers; (b) a first population of electrically excitable cells immobilized at a first cell seeding domain on the scaffold; (c) a second population of electrically excitable cells immobilized at a second cell seeding domain on the scaffold at a site that is distinct from the first cell seeding domain; and (d) at least first and second aligned nanofibrous conduits provided on a surface of the unaligned nanofibers, wherein the first conduit is in contact with the first cell seeding domain, and the second conduit is in contact with the second cell seeding domain, and wherein the first conduit and second conduit contact each other at an intersection, and wherein the electrically excitable cells form synapses at the intersection.

In accordance with inventive principles, electrically excitable cells are cultured on a surface of the nanofibrous scaffold in a manner that mimics the natural environment of the cells. This is provided by the architecture of the scaffold, as well as chemical properties.

In accordance with inventive concepts, electrically excitable cells are immobilized in a manner such that the cells can form a functional synaptic network, thereby generating an open field potential. To accomplish this, the scaffold provides discrete cell seeding domains that are not in contact with each other, but rather are connected via dedicated conduits that originate at a specific cell seeding domain and irradiate from that domain. Each conduit then contacts another conduit at an intersection. This intersection thus provides a location for the distinct populations of cells to communicate with one another. Such communication can take place through formation of synapses at the intersection. In some embodiments, the axons of one population of cells may synapse with a second population of cells on their soma (for example, with unipolar cells lacking dendrites). In other words, the neurites/axons of a first population may be able to turn at the intersection of conduits and continue on to the second population and form synapses at the second cell seeding domain instead.

In accordance with inventive concepts, electrically excitable cells generate an electric field that is polarized. In some aspects, synapses are preferably located on the scaffold in a manner such that the generated charge can be measured (i.e., localized charges do not cancel each other out). In some implementations, nanofiber conduits provide neurite guidance cues, and these guidance cues direct neurite growth in direction away from cell bodies toward an intersection that is separated from the cell seeding domains.

Electrically excitable cells are immobilized at discrete cell seeding domains on the scaffold. Thus, in some implementations, inventive concepts provide devices and methods for co-culture of at least two populations of electrically excitable cells.

A first population of electrically excitable cells immobilized at a first cell seeding domain on the scaffold, and a second population of electrically excitable cells immobilized at a second cell seeding domain on the scaffold at a site that is distinct from the first cell seeding domain. Optionally, additional cell seeding domains can be provided (for example, second, third, fourth, and so on), as desired. Inventive concepts thus provide significant flexibility in creating a culture environment for desired cell populations.

Each cell seeding domain is provided at a distinct site on the scaffold. In this manner, each cell population can grow in a distinct domain on the scaffold surface. The cell seeding domains on the scaffold surface can be provided in any predetermined geometry. In general, the pattern includes at least two areas of sufficient size for the adhering of a cell body (soma), preferably a neuronal cell body. These cell-body or somal areas are interconnected via nanofibrous conduits of sufficient dimensions to provide for adhesion of at least one axon or dendrite. For hippocampal neurons, the somal region is about 5-25 µm in diameter. The cell seeding domain comprises a cell-adherent surface, preferably comprising poly-D-lysine and is that area of the scaffold to which the neuron cell-body attaches.

Inventive scaffolds include at least first and second aligned nanofibrous conduits that are provided on a surface of the unaligned nanofibers. The first conduit is in contact with the first cell seeding domain, and the second conduit is in contact with the second cell seeding domain, and the first conduit and second conduit contact each other at an intersection, and wherein the electrically excitable cells form synapses at the intersection. The nanofibrous conduits thus provide a roadmap for fabricating a cell network that incorporates the cells of the first cell seeding domain and the cells of the second cell seeding domain.

Connected to the cell seeding domain is at least one nanofibrous conduit, of sufficient dimension to provide for the growth and adhesion of an axonal or dendritic processes.

For rat hippocampal neurons, for example, the width of the conduit is generally up to about 300 μm in width, or up to about 250 μm, or up to about 200 μm, or up to about 100 μm, in width.

Optionally, the nanofibrous conduit includes a cell-adherent or growth factor surface to modulate the growth of neurites, axons, dendrites, or their support cells.

Illustrative cell-adherent materials for the cell seeding and/or nanofibrous conduits include extracellular matrix components, proteins (such as gelatin), and cell attachment polymers (such as poly-D-lysine, poly-L-lysine, acrylates, and hydrogels). Illustrative extracellular matrix components include glycosaminoglycans and their proteoglycans, adhesive glycoproteins, and fibrous proteins. Suitable glycosaminoglycans include, but are not limited to, hyaluronan, chondroitin sulfate, dermatan sulfate, keratan sulfate, and heparin sulfate. Exemplary proteoglycans include small interstitial proteoglycans (such as decori, biglyca); aggrecan family (such as aggrecan, brevican, neurocan, versican); HS proteoglycans (such as periecan, agrin, syndecans, betaglycan, glypicans, serglycin); and KS proteoglycans (such as lumican, keratocan, fibromodulin, mimecan, SV2, claustrin). Illustrative adhesive glycoproteins include, but are not limited to, laminin, fibronectin, tenascin, and nidogen). Exemplary fibrous proteins include collagens and elastin. In further embodiments, cell-adherent materials for the cell seeding and/or nanofibrous conduits comprise biological molecules that stimulate the growth of nerve cells, for example, BDNF, NGF or GDNF.

In some implementations, inventive scaffold can include a passivating agent. Such passivating agent can surround the cell seeding domains and/or the nanofibrous conduits. Passivation, in biochemistry and cell biology, refers to a material becoming "passive," that is, being less prone to interact with biological systems. It can involve a shielding outer layer of material which can be applied as a coating. Passivation is useful to reduce the degree of chemical adsorption (particularly protein adsorption), cellular attachment, cellular proliferation, and cellular growth including the growth or extension of cell processes such as neurites, filopodia, and lamellipodia. Thus, passivating agents can enhance the ability to separate cell seeding domains in a manner such that cellular networks mimicking the function of native tissue can be formed. Illustrative passivating agents include materials that can repel adherence of cells to the scaffold, such as polyethylene glycol (PEG).

As used herein, the term "scaffold" refers to a 3-dimensional substrate to provide structural support for cells, such as mammalian cells. The scaffold may become a tissue supporting substrate and may be an electrically conductive. In some implementations, the scaffold comprises unaligned nanofibers. Optionally, the unaligned nanofibers can be randomly oriented, such as in a nonwoven mat.

In some implementations, nanofibrous scaffolds are composed of multiple layers of nanofibers. One or more layers of the nanofibers can be composed of aligned nanofibers, while one or more layers can be composed of unaligned nanofibers.

Nanofibers typically have a diameter ranging from about 1 nm to about 100 nm and may have a diameter ranging from about 1 nm to about 1000 nm. Although discussion herein will focus on use of nanofibers to form scaffolds, it will be understood that microfibers can also be used in accordance with inventive concepts. Microfibers are fibers larger than nanofibers and have a diameter in the range of about 1 to about 5 microns, or about 1 to 10 microns. Nanofibers and microfibers can provide high surface area, small fiber diameter, layer thinness, high permeability, and low basis weight.

A number of processing techniques such as drawing, template synthesis, phase separation, self-assembly or electrospinning have been used to prepare nanofibers. Nanofibers and microfibers may be fabricated by electrostatic spinning (also referred to as electrospinning). The technique of electrospinning of liquids and/or solutions capable of forming fibers, is well known and has been described in a number of patents, such as, for example, U.S. Pat. Nos. 4,043,331 and 5,522,879. Electrospinning generally involves the introduction of one or more polymeric materials or other fiber-forming solutions or liquid into an electric field, so that the solution or liquid produces nanofibers. When a strong electrostatic field is applied to a fiber-forming combination held in a syringe with a capillary outlet, a pendant droplet of the fiber-forming combination from the capillary outlet is deformed into a Taylor cone. When the voltage surpasses a threshold value, the electric forces overcome the surface tension on the droplet, and a charged jet of the solution or liquid is ejected from the tip of the Taylor cone. The ejected jet then moves toward a collecting metal screen that acts as a counter electrode having a lower electrical potential. The jet is split into small charged fibers or fibrils and any solvent present evaporates leaving behind a nonwoven mat formed on the screen.

In one embodiment, the electrospun fiber compositions comprise randomly oriented fibers. In alternative embodiments, the compositions comprise aligned fibers. The electrospun fiber compositions can be produced by electrospinning methods known in the art, e.g., uniaxial electrospinning, coaxial electrospinning or multiaxial electrospinning.

As used herein, the term "uniaxial electrospinning" is intended to mean the electrospinning of a single electrospinning solution supply that is dispensed from a single spinneret.

As used herein, the term "coaxial electrospinning" is intended to mean the electrospinning of a single electrospinning solution supply that comprises of two different solutions that are physically separated from each other and that are dispensed from two separate spinnerets that share the same axis of symmetry.

As used herein, the term "multiaxial electrospinning" is intended to mean the electrospinning of a single electrospinning solution supply that comprises of multiple solutions that are physically separated from each other and that are dispensed through multiple spinnerets that share the same axis of symmetry.

Electrospinning parameters can be readily adjusted with routine experimentation. For example, other collectors, such as rotating drum-type collectors, can be used to generate aligned fibers. The supply voltage, collector distance, polymer concentration, and solution flow rate can be adjusted to achieve the desired pore size and/or fiber diameters.

The process of electrostatic spinning has typically been directed toward the use of the fibers to create a mat or other non-woven material, as disclosed, for example, in U.S. Pat. No. 4,043,331. Fibers ranging from 50 nm to 5 μ in diameter can be electrospun into a nonwoven fiber mesh or an aligned nanofiber array. Due to the small fiber diameters, electrospun textiles inherently possess a very high surface area and a small pore size. These properties make electrospun fabrics potential candidates for a number of applications including: membranes, tissue scaffolding, and other biomedical applications.

In some implementations, a fiber includes one or more natural or synthetic polymeric material. According to various embodiments of the present invention, the polymeric material of the nanofiber may be hydrophilic, hydrophobic, amphiphilic, thermally responsive, or electrically conductive, depending on the desired application. According to yet a further embodiment of the present invention, the nanofiber also may include biodegradable and/or non-biodegradable polymers.

A "synthetic polymer" refers to a polymer that is synthetically prepared and that includes non-naturally occurring monomeric units. For example, a synthetic polymer can include non-natural monomeric units such as acrylate or acrylamide units. Synthetic polymers are typically formed by traditional polymerization reactions, such as addition, condensation, or free-radical polymerizations. Synthetic polymers can also include those having natural monomeric units, such as naturally-occurring peptide, nucleotide, and saccharide monomeric units in combination with non-natural monomeric units (for example synthetic peptide, nucleotide, and saccharide derivatives). These types of synthetic polymers can be produced by standard synthetic techniques, such as by solid phase synthesis, or recombinantly.

A "natural polymer" refers to a polymer that is either naturally, recombinantly, or synthetically prepared and that consists of naturally occurring monomeric units in the polymeric backbone. In some cases, the natural polymer may be modified, processed, derivatized, or otherwise treated to change the chemical and/or physical properties of the natural polymer. In these instances, the term "natural polymer" will be modified to reflect the change to the natural polymer (for example, a "derivatized natural polymer", or a "deglycosylated natural polymer").

Nanofiber materials, for example, may include both addition polymer and condensation polymer materials such as polyolefin, polyacetal, polyamide, polyester, cellulose ether and ester, polyalkylene sulfide, polyarylene oxide, polysulfone, modified polysulfone polymers and mixtures thereof. Exemplary materials within these generic classes include polyethylene, poly($\varepsilon$-caprolactone), poly(lactate), poly(glycolate), polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinyl alcohol in various degrees of hydrolysis (87% to 99.5%) in crosslinked and non-crosslinked forms. Exemplary addition polymers tend to be glassy (a Tg greater than room temperature), such as polyvinylchloride, polymethylmethacrylate, and polystyrene polymer compositions. Other addition polymers include syndiotactic polystyrene, copolymers of vinylidene fluoride and hexafluoropropylene, polyvinyl acetate, amorphous addition polymers, such as poly(acrylonitrile) and its copolymers with acrylic acid and methacrylates.

In some embodiments of the invention the nanofiber material is a polyamide condensation polymer. In more specific embodiments, the polyamide condensation polymer can be a nylon polymer. The term "nylon" is a generic name for all long chain synthetic polyamides. Copolymers can be made by combining various diamine compounds, various diacid compounds and various cyclic lactam structures in a reaction mixture and then forming the nylon with randomly positioned monomeric materials in a polyamide structure. Illustrative polymers include nylon-6,6; nylon-6,9; nylon-6,10; nylon-6,12; nylon-11; nylon-12; and nylon-4,6.

Block copolymers can also be used as nanofiber materials. In formulating a composition for the preparation of nanofibers, a solvent system can be chosen such that both blocks are soluble in the solvent. One example is an ABA (styrene-EP-styrene) or AB (styrene-EP) polymer in methylene chloride solvent. Examples of such block copolymers are a Kraton™ type of AB and ABA block polymers including styrene/butadiene and styrene/hydrogenated butadiene(ethylene propylene), a Pebax™ type of epsilon-caprolactam/ethylene oxide and a Sympatex™ type of polyester/ethylene oxide, and polyurethanes of ethylene oxide and isocyanates.

Nanofibers can also be formed from polymeric compositions comprising two or more polymeric materials in polymer admixture, alloy format, or in a crosslinked chemically bonded structure. Two related polymer materials can be blended to provide the nanofiber with beneficial properties. For example, a high molecular weight polyvinylchloride can be blended with a low molecular weight polyvinylchloride. Similarly, a high molecular weight nylon material can be blended with a low molecular weight nylon material. Further, differing species of a general polymeric genus can be blended. For example, a high molecular weight styrene material can be blended with a low molecular weight, high impact polystyrene. A Nylon-6 material can be blended with a nylon copolymer such as a Nylon-6, Nylon-6,6, or Nylon-6,10 copolymer. Further, a polyvinyl alcohol having a low degree of hydrolysis such as a 87% hydrolyzed polyvinyl alcohol can be blended with a fully or super hydrolyzed polyvinyl alcohol having a degree of hydrolysis between 98% and 99.9%, and higher. All of these materials in admixture can be crosslinked using appropriate crosslinking mechanisms. Nylons can be crosslinked using crosslinking agents that are reactive with the nitrogen atom in the amide linkage. Polyvinyl alcohol materials can be crosslinked using hydroxyl reactive materials such as monoaldehydes, such as formaldehyde, ureas, melamine-formaldehyde resin and its analogues, boric acids, and other inorganic compounds, dialdehydes, diacids, urethanes, epoxies, and other known crosslinking agents. Crosslinking agents react and form covalent bonds between polymer chains to substantially improve characteristics such as molecular weight, chemical resistance, overall strength and resistance to mechanical degradation.

Biodegradable polymers can also be used in the preparation of fibers. Examples of classes of synthetic polymers that have been studied as biodegradable materials include polyesters, polyamides, polyurethanes, polyorthoesters, polycaprolactone (PCL), polyiminocarbonates, aliphatic carbonates, polyphosphazenes, polyanhydrides, and copolymers thereof. Specific examples of biodegradable materials include, for example, polylactide, polyglycolide, polydioxanone, poly(lactide-co-glycolide), poly(glycolide-co-polydioxanone), polyanhydrides, poly(glycolide-co-trimethylene carbonate), and poly(glycolide-co-caprolactone). Blends of these polymers with other biodegradable polymers can also be used.

In some implementations, the nanofibers can include one or more components that provide features to the scaffold. Illustrative components include crosslinking agents having latent reactive or chemically reactive groups; surface coatings; and/or bioactive agents.

The nanofiber components can be dissolved in any solvent that allows delivery of the compounds to the orifice, tip or a syringe, under conditions that the compound is electrospun. Solvents useful for dissolving or suspending a material or a substance will depend upon the compound.

In some implementations, different polymers can be used to fabricate nanofibers within the same scaffold. By varying the composition of the fibers being electrospun, it will be appreciated that fibers having different physical or chemical properties can be obtained. This can be accomplished either by spinning a liquid containing a plurality of components, each of which can contribute a desired characteristic to the finished product, or by simultaneously spinning fibers of different compositions from multiple liquid sources, that are then simultaneously deposited to form a matrix. The resulting matrix comprises layer of intermingled fibers of different compounds. The plurality of layers of different materials can convey a desired characteristic to the resulting composite matrix with each different layer providing a different property.

The electrospun nanofiber composite has an ultrastructure with a three-dimensional network that supports cell growth, proliferation and activity. This three-dimensional network is similar to the environment where many of these excitable cells naturally occur, for example, in the brain. The spatial distance between the fibers can play an important role in cells being able to obtain nutrients for growth as well as for allowing cell-cell interactions to occur.

In some implementations, a nanofiber includes one or more natural or synthetic polymeric material and one or more crosslinking agent, each crosslinking agent having at least two latent reactive groups or chemically reactive groups. Latent reactive groups include photochemically and thermally reactive groups, each of which will form covalent bonds when subjected to a source of energy. Suitable energy sources include radiation and thermally energy. In some embodiments, the radiation energy is visible, ultraviolet, infrared, x-ray or microwave electromagnetic radiation.

In general, latent reactive groups are chemical entities that respond to specific applied external energy or stimuli to generate active species with resultant covalent bonding to an adjacent chemical structure. Latent reactive groups are those groups that retain their covalent bonds under storage conditions but that form covalent bonds with other molecules upon activation by an external energy source. In some embodiments, latent reactive groups form active species such as free radicals. These free radicals may include nitrenes, carbines or excited states of ketones upon absorption of externally applied electric, electrochemical or thermal energy. Various examples of known or commercially available latent reactive groups are reported in U.S. Pat. Nos. 4,973,493; 5,258,041; 5,563,056; 5,637,460; and 6,278,018.

When a latent reactive group is provided in the material forming the nanofiber, the resulting composition is a latent reactive nanofiber. Such latent reactive nanofibers and methods of preparing them are described, for example, in U.S. Pat. No. 8,709,809 B2 (Wen et al., Apr. 29, 2014). Latent reactive nanofibers can be used to provide a scaffold with an architecture to provide a functionalized surface on a scaffold that is optimized for extracellular field recording techniques.

In some implementations, the crosslinking agent can be selected from those described in U.S. Pat. No. 7,772,393 (Guire et al., Aug. 10, 2010), U.S. Pat. No. 8,487,137 (Guire et al., Jul. 16, 2013), U.S. Pat. No. 8,779,206 (Guire et al., Jul. 15, 2014), U.S. Pat. No. 7,989,619 (Guire et al., Aug. 2, 2011), U.S. Pat. No. 8,496,857 (Guire et al., Jul. 30, 2013), and U.S. Publication No. 2014/0011938 A1 (Guire et al., Jan. 9, 2014). The crosslinking agents described in these patents utilize benzophenone photochemistry, which can form covalent, carbon-carbon bonds between practically any two hydrocarbon-based materials upon exposure to ultraviolet light of the appropriate wavelength. Bond formation proceeds efficiently through a process known as hydrogen abstraction.

In some implementations, latent reactive groups comprise photoactivatible groups. There are generally three types of crosslinking materials with photoactivatable groups. One type is hydrophobic in nature, making it difficult to dissolve in an aqueous systems. The second type is hydrophilic, but includes quaternary charged moieties. Quaternary compounds tend to promote non-specific binding of non-target molecules, which is often not a desired result. A third type of crosslinking material with photoactivatable groups includes negatively "charged" groups, such as carboxylic acids, sulfonic acids, phosphoric acids and the like. Although these materials are considered to be hydrophilic, they also increase non-specific binding interactions with non-targeted molecules by the crosslinking material.

Latent reactive groups that are reactive to electromagnetic radiation, such as ultraviolet or visible radiation, are typically referred to as photochemical reactive groups or photoactivatible groups.

Photoreactive species are as described herein, and are sufficiently stable to be stored under conditions in which they retain such properties. See, e.g., U.S. Pat. No. 5,002, 582. Latent reactive groups can be chosen that are responsive to various portions of the electromagnetic spectrum, with those responsive to ultraviolet and visible portions of the spectrum (referred to herein as "photoreactive") in particular.

Photoreactive species respond to external stimuli and undergo active specie generation with the formation of a covalent bond to an adjacent chemical structure, for example, as provided by the same or a different molecule. Photoreactive species are those groups of atoms in a molecule that retain their covalent bonds during storage but, upon activation by an external energy source, form covalent bonds with other molecules.

Photoreactive species generate active species such as free radicals and particularly nitrenes, carbenes, and excited states of ketones upon absorption of electromagnetic energy. Photoreactive species can be chosen to be responsive to various portions of the electromagnetic spectrum, and photoreactive species that are responsive to e.g., ultraviolet and visible portions of the spectrum, are referred to as a "photochemical group" or "photogroup."

The use of photoreactive species in the form of photoreactive aryl ketones are useful, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthene, thioxanthone, anthraquinone, aryl azide, aryl ketone, aryl ketone derivative, halophenyl azide, and their ring substituted derivatives. In particular, thioxanthone, and its derivatives, having excitation energies greater than about 360 nm are useful.

The functional groups of such ketones are suitable because they are readily capable of undergoing an activation/inactivation/reactivation cycle. Benzophenone is an exemplary photochemically reactive activatable group, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photochemically reactive activatable aryl ketones such as benzophenone and acetophenone are of particular importance inasmuch as these groups are subject to multiple reactivation in water and hence provide increased bonding efficiency. Other illustrative latent reactive groups include photoactivatible phenyl azides, perhalophenyl azides, and diazerines.

In some implementations, latent reactive groups comprise thermally reactive groups. In general, latent reactive groups that are reactive to thermal (or heat) energy include a variety of reactive moieties, and may include known compounds that decompose thermally to form reactive species that will then form covalent bonds. The covalent bonds allow the crosslinking to bind to adjacent materials. Suitable thermally-reactive groups typically have a pair of atoms having a heat sensitive or labile bond. Heat labile bonds include oxygen-oxygen bonds such as peroxide bonds, nitrogen-oxygen bonds, and nitrogen-nitrogen bonds. Such bonds will react or decompose at temperatures in a range of not more than 80-200° C. Perfluorophenyl azides are examples of thermally reactive groups (as well as photoreactive).

Both thermally generated carbenes and nitrenes undergo a variety of chemical reactions, including carbon bond insertion, migration, hydrogen abstraction, and dimerization. Examples of carbene generators include diazirines and diazo-compounds. Examples of nitrene generators include aryl azides, particularly perfluorinated aryl azides, acyl azides, and triazolium ylides. In addition, groups that upon heating form reactive triplet states, such as dioxetanes, or radical anions and radical cations may also be used to form the thermally-reactive group.

In one embodiment the thermally-reactive group of the crosslinking agent includes a peroxide —(O—O)— group. Thermally-reactive peroxide-containing groups include, for example, thermally-reactive diacyl peroxide groups, thermally-reactive peroxydicarbonate groups, thermally-reactive dialkylperoxide groups, thermally-reactive peroxyester groups, thermally-reactive peroxyketal groups, and thermally-reactive dioxetane groups.

Dioxetanes are four-membered cyclic peroxides that react or decompose at lower temperatures compared to standard peroxides due to the ring strain of the molecules. The initial step in the decomposition of dioxetanes is cleavage of the O—O bond, the second step breaks the C—C bond creating one carbonyl in the excited triplet state, and one in an excited singlet state. The excited triplet state carbonyl can extract a hydrogen from an adjacent material, forming two radical species, one on the adjacent material and one on the carbon of the carbonyl with the oxygen and will form a new covalent bond between the thermally reactive dioxetane and the adjacent material.

Representative thermally reactive moieties are reported in U.S. Pat. No. 7,507,750 (Taton et al., Oct. 5, 2010) and U.S. Pat. No. 5,258,041 (Guire et al., Nov. 2, 1993).

The crosslinking agent may have at least two latent reactive activatable groups. These latent reactive groups may be the same or may be different. For example, all of the latent reactive groups may be photochemically reactive groups. Alternatively, in other embodiments of the invention the crosslinking agent may include both photochemically and thermally reactive groups. Further, the crosslinking agent may be monomeric or polymeric materials or may be a mixture of both monomeric and polymeric materials.

In some embodiments, the latent reactive groups of a particular crosslinker are the same, while in other embodiments the latent reactive groups may be different. For example, the latent reactive groups may be two different groups that are both activated by radiation. In other embodiments one latent reactive group may be activated by radiation while another latent reactive group may be activated by heat. Suitable crosslinking agents include bi-, tri- and multi-functional monomeric and polymeric materials.

In particular, there are known crosslinking materials that include a latent reactive group, such as a photoactivatable group. The crosslinking material has, in general, at least two photoactivatable groups, such that one group can be activated and attached to the surface of the substrate. The remaining latent group, can then later be, or simultaneously with the surface attachment, activated to react with a target molecule such as a polymer or a biomolecule.

According to another embodiment of the invention, a latent reactive activatable nanofiber is produced by combining one or more polymeric materials with one or more crosslinking agents each having at least two latent reactive activatable groups and forming at least one nanofiber from the combination. The nanofiber may be formed by electrospinning the combination containing the polymeric materials and the crosslinking agent. The use of photoreactive nanofibers enables an easy, precise, and efficient method for photo-patterned surface modification with multiple natural or synthetic extracellular matrix components, including growth factors and their gradients. Photopatterning can be achieved, prior to stacking and annealing the fiber mats, through the use of static or mobile opaque photomasks. Such photoreactive nanofibers are non-cytotoxic and have a pore size that allows excellent cell penetration.

In some implementations, the nanofibers include one or more chemically reactive groups. When included, the chemically reactive groups can be provided on the surface of the fiber, can be pendent to the chemical backbone of the polymer used to fabricate the nanofiber, can be coupled to the fiber via the latent reactive group(s) of the nanofiber, or other suitable mechanisms. Illustrative chemically reactive groups include, but are not limited to, carboxy, ester, epoxy, hydroxyl, amino, amino, thiol, N-hydroxy succinimide, isocyanate, anhydride, azide, aldehyde, cyanuryl chloride or phosphine groups, and the like.

Other chemically reactive groups include complementary chemically reactive groups, such as those used in click chemistry. As used herein, "click chemistry" refers to reactions that involve pairs of functional groups that rapidly and selectively react ("click") with each other in mild, aqueous conditions. Click chemistry reactions can he categorized into two separate groups: Copper (Cu(I))-catalyzed and Copper-free. The Cu(I)-catalyzed azide-alkyne click chemistry reaction relies on the presence of Cu(I) ions whereas the Copper-free reactions proceed without metal catalysis (such as the Staudinger Ligation, copper-free azide-phosphine reaction). Additional chemically reactive groups include high-affinity ligand pairs such as avidin-biotin and cyclodextrin-adamantane. Such chemically reactive groups can provide a means to covalently modify the surface of the fibers with natural or synthetic molecules to control the attachment, growth, morphology, or differentiation of cells.

In preferred embodiments, the scaffold comprises a bioactive agent. For purposes of the description herein, reference will be made to "bioactive agent," but it is understood that the use of the singular term does not limit the application of bioactive agents contemplated, and any number of bioactive agents can be provided using the teaching herein. As used herein, "bioactive agent" refers to an agent that affects physiology of biological tissue. Bioactive agents useful according to the invention include virtually any substance that possess desirable characteristics to the scaffolds described herein.

When included, the bioactive agent(s) can be provided on the surface of nanofibers used to fabricate the scaffold. For example, bioactive agents can be coupled to the fiber via the latent reactive group(s) and/or chemically reactive groups of the nanofiber. Alternatively, bioactive agents can be provided in the nanofibers themselves, for example, by including them as pendent to the chemical backbone of the polymer used to fabricate the nanofiber and/or combining the bioactive agent(s) with other materials (e.g., by mixing) prior to electrospinning the nanofiber composition.

Illustrative bioactive agents include, but are not limited to, polyethylene glycol (PEG). Other bioactive agents include enzyme inhibitors, modulators of cell-extracellular matrix interactions including cell growth inhibitors and anti-adhesion molecules, and inhibitors of DNA, RNA or protein synthesis.

One type of bioactive agent that can be used is a cell culture agent. Illustrative cell culture agents include, but are not limited to, cell attachment, growth, proliferation, or differentiation agents, or a combination of any two or more of these. In some implementations, molecules that stimulate the growth and/or adhesion of cells on the scaffold can be used. :For neural cells, proteins such as serum albumin, laminin, tenascin, NCAM, L1, bFGF and GAGs can be used.

Laminin, tenascin, NCAM and L1 cause interactions with the extracellular matrix of various tissues. Laminin encourages neuronal growth and the branching of micro-glia. NCAM may be able to induce proliferation of neurons. Tenascin has been shown to be repulsive to neurons and glia and may be useful as a derivatization of cell-repelling regions. L1 has been shown to encourage axonal migration and can therefore be useful as a derivatization of regions supporting axonal growth.

The growth factors bFGF and BDNF are known to be used in the signal transduction pathways leading to cellular differentiation and have been shown to promote neuronal survival in culture.

The GAG polysaccharides represent the other major class of extracellular macromolecules that make up the ECM.

In some implementations, gradients of bioactive agents can be provided on the scaffold surface. Such gradients can comprise differing concentration of bioactive agent across an area of the scaffold. The different concentrations can be provided by different concentration of bioactive agent included within nanofibers used to fabricate a particular area of the scaffold, and/or by coupling different amounts of bioactive agent to the surface of the scaffold (for example, using latent reactive and/or chemically reactive groups in the nanofibers).

According to yet a further embodiment of the present invention, nanofibers may be further combined with a functional polymer that will subsequently react with biologically active materials. Functional polymers include any suitable polymer having one or more functional groups that will react with a biologically active material and/or biologically passivating materials. Representative functional groups for these polymers include carboxy, ester, epoxy, hydroxyl, amido, amino, thio, N-hydroxy succinimide, isocyanate, anhydride, azide, aldehyde, cyanuryl chloride or phosphine groups.

In some implementations, the scaffold includes a microscale or a nanoscale topography that modulates cell growth or proliferation. In accordance with these aspects, the topography of the scaffold can provide the communication network for cells seeded on the scaffold. Such topography can be formed, for example, by three-dimensional printing, also known as additive manufacturing.

Figure 6:
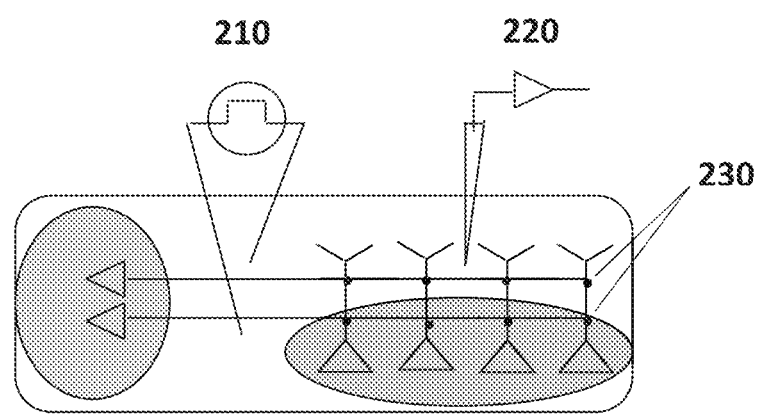
FIG. 6 is a schematic representation of an illustrative bioartificial scaffold containing cultures of two cell populations, with stimulating and extracellular field recording electrodes.
Figure 11:
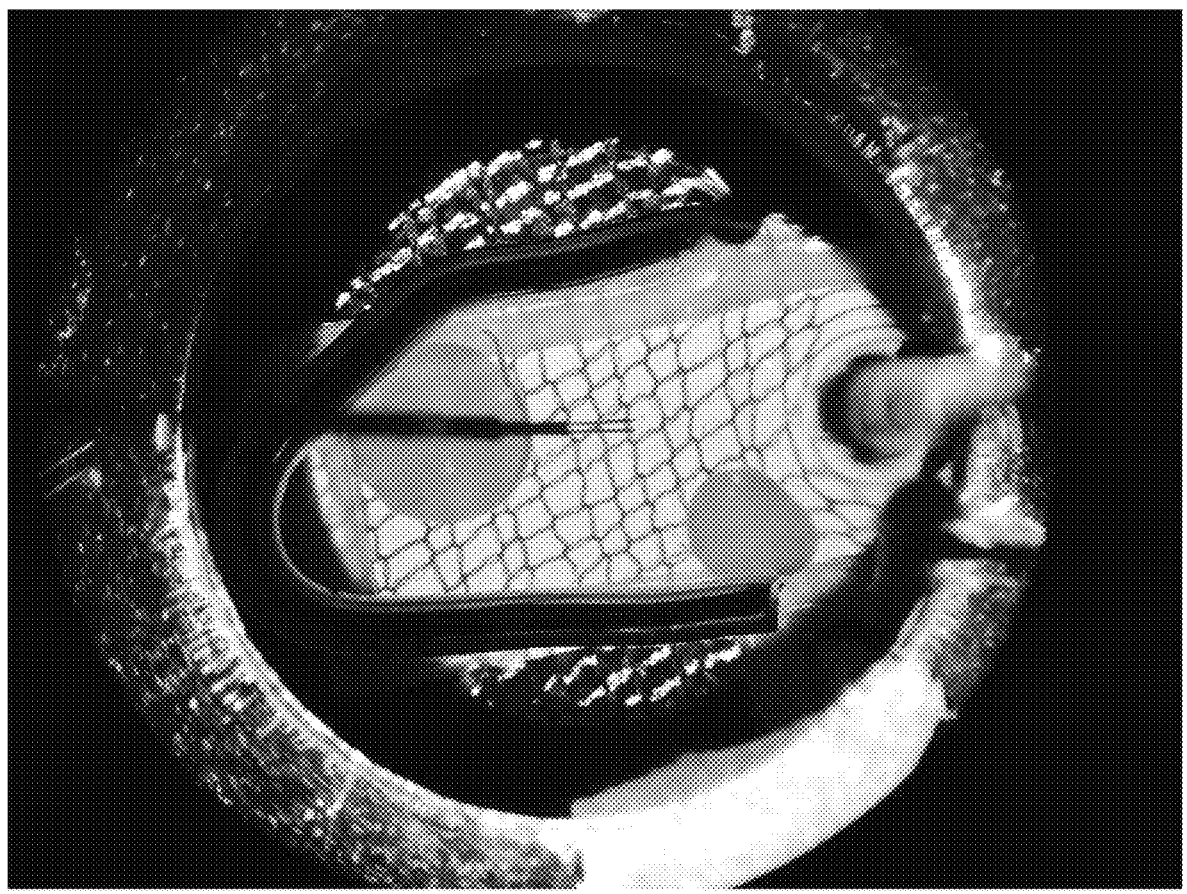
FIG. 11 is a photomicrograph of a bioartificial open field tissue scaffold in a conventional field recording chamber. Scaffold size is 4×8 mm, excluding the frame.

In some implementations, the scaffold can further include at least one electrode operably coupled to scaffold. The electrode can be utilized to measure field potentials generated by the scaffold. One illustrative embodiment of these aspects is shown in FIG. 6. As illustrated, a stimulating electrode 210 can be provided in association with a scaffold, as well as a recording electrode 220. Chemical synapses between the cell populations are shown at spots 230. A photomicrograph of such an arrangement is also shown in FIG. 11.

In some implementations, the scaffold can further comprise a support selected from petri dishes, flasks, multiwell plates, slides, films, frames, and hydrogels. The support can be fabricated from any of a large variety of non-cytotoxic solids and gels. Illustrative support material includes, but is not limited to, silicones, polyolefins, vinyl polymers, polystyrenes, polyacrylates, poly methacrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, phenolics, amino-epoxy resins, polyesters, polyethers, cellulose-based plastics, rubber-like plastics, copolymers, or any mixtures or combinations thereof. Other suitable support materials include silica glass, alginate, collagen, various hydrogels, self-assembled nanofibers, proteins, nucleic acids, polysaccharides, drawn or spun nanofibers, synthetic extracellular matrix, animal and plant extracts, and the like.

Inventive concepts pertain to development of a novel closed culture device for maintenance of excitable cells using nanofiber scaffold composites incorporated within the closed culture device. Existing closed culture devices largely consist of flat plastic culture surfaces (such as tissue culture treated polystyrene, TCPS) that do not adequately mimic the native environments where excitable cells reside in vivo. Inventive concepts described herein represent significant advancements in the field by providing a closed culture device that incorporates a culture substrate capable of better mimicking the native excitable cell niche, and thereby providing improved screening models.

In some implementations, electrospun nanofiber composites are attached directly to a culture container. In further embodiments, nanofiber composites can be attached to a substrate (such as an acetal frame, Example 4) prior to incorporation within a culture container. Nanofiber composites can be attached to the culture container or a substrate through chemical (e.g., adhesive) or non-chemical (e.g., thermal bonding or annealing) means.

In some implementations, the culture container can be composed of gas permeable materials (such as EVA, EVO). In alternative implementations, the culture container can be composed of materials that are minimally-permeable (such as polystyrene, FEP).

In some implementations, the culture container can include one inlet/outlet valve (in the form of tubing, spike connector, luer fittings, and the like) for culture medium and reagents injection, as well as cell harvesting. In other implementations, the culture container can include two, three or four such inlet/outlet valves.

In further implementations, the cell culture container can include and a stimulating electrode and/or recording electrode, for electrophysiological measurements. Future generations of this technology can include integrated multielectrode arrays to increase the convenience and enhance the resolution of field recordings, resulting in more robust data collection. As envisioned, the assembled scaffolds will be available as kits and systems with protocols for generating defined neural circuits, tailored to model synaptic pairs of interest and derived from cell lines.

In certain implementations, cell culture containers can allow for automated control of oxygen levels carbon dioxide levels, temperature, pH levels, and the level of cell waste including ammonia or other ammonia related waste products referred to as ammoniac. In accordance with these aspects, the device allows probes to be inserted within the device for continuous monitoring of oxygen, carbon dioxide, temperature, pH and accumulation of culture waste. Such probes can be additionally connected to a computer terminal that analyzes the incoming data and outputs signals that control operation of pumps and valves to inject appropriate reagents into the device. Reservoirs of culture media, gas, and pH control reagents can be connected via closed loops to the culture device to maintain sterile conditions during culturing and/or assay.

In an embodiment, the bioartificial brain slice scaffold is a laminated, 3-dimensional nanofiber scaffold for co-cultures of two distinct human neural populations which exhibit the desired pre- and postsynaptic neuronal and glial phenotypes. Through surface modification, such as photopatterning, and control over nanofiber topography, the blueprint for a tightly defined synaptic circuit capable of generating an extrasynaptic field potential in response to orthodromic stimulation will be contained within the scaffolds. The scaffold support should also prevent thinning, spreading, and other tissue morphology changes characteristic of organotypic slices, where extracellular field recording is more challenging.

Figure 2:
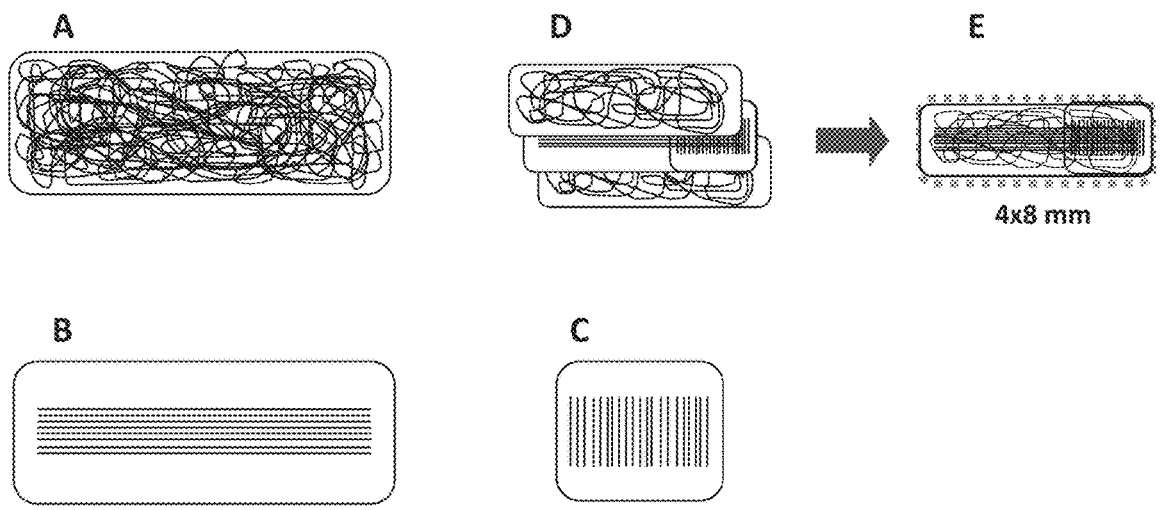
FIG. 2 is a schematic representation of illustrative photoreactive nanofiber scaffold components and assembly.

In some aspects, inventive methods for preparing a scaffold are provided. One illustrative method is shown in FIG. 2. Such methods can involve steps of generating nanofiber mats that are aligned and unaligned, and laminating these mats together to form a scaffold composite. Methods of producing aligned and unaligned nanofibers are described elsewhere herein. FIG. 2A shows nonwoven photoreactive nanofiber mats (pore size>5 microns) that can serve as an artificial extracellular matrix for cell attachment and growth. Parallel nanofibers (FIGS. 2B and 2C) can guide neurite outgrowth and axonal extension. FIG. 2D, illustrates one technique of stacking nanofiber mats in alternating layers, thereby producing a scaffold that has a total thickness of about 350 microns, for example. The laminated mats can be cut and annealed at the edges using a heated die, as illustrated in FIG. 2E. Optionally, each layer of the scaffold (e.g., 2A, 2B, and/or 2C) can have multiple patterned gradients, to support cellular attachment, differentiation, and growth of hNPs and glia.

In some implementations, there are provided methods for producing a nanofibrous scaffold composite comprising steps of: (a) providing a nanofibrous scaffold; (b) providing a cell culture agent at two or more distinct domains on a surface of the scaffold, thereby forming two or more distinct cell seeding domains; (c) disposing two or more aligned nanofibrous conduits on the scaffold surface, in a configuration so that each conduit is in contact with one cell seeding domain, and each conduit intersects the other conduit at an intersection located separate from the cell seeding domains; and (d) culturing electrically excitable cells on the distinct cell seeding domains under conditions to form functional chemical synapses between the electrically excitable cells.

As discussed elsewhere herein, the nanofibrous scaffold can be generated using electrospinning or other suitable method. Cell culture agent can be providing at the cell seeding domains by any of the methods described herein. For example, the cell culture agent can be coupled to the surface of the cell seeding domains via latent reactive or chemically reactive groups included in the nanofibers forming the cell seeding domains. Alternatively, cell culture agent can be mixed with the material forming the nanofibers, thereby providing the cell culture agent throughout the material of the nanofiber. Still further, the cell culture agent can be applied to the surface of cell seeding domains in any suitable manner, including spraying, dipping, injecting, infusing, and/or brushing the cell culture agent onto the scaffold.

Figure 5:
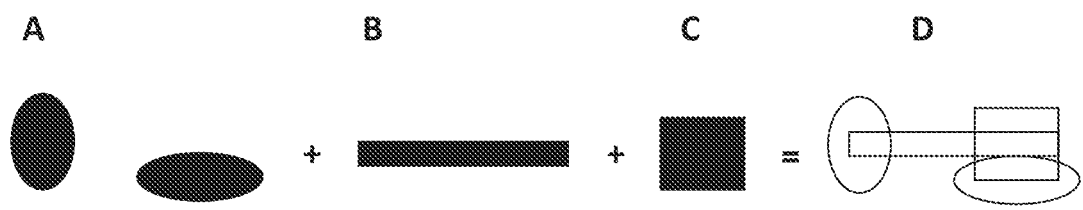
FIG. 5 is a schematic representation of illustrative assembly of photolithographic masks to prepare a patterned scaffold for use with co-culture of brain cells.

Optionally, a passivating polymer can be provided to an area of the scaffold outside the cell seeding domains. In some embodiments, passivating polymer is applied to the scaffold in conjunction with a photomask. As used herein, "photomask" refers to an opaque area with holes or transparencies that allow light or other treatments to penetrate through in a defined pattern. Masks can be provided in a variety of shapes such as oval, rectangular, and the like. FIG. 5 shows representative photomasks in one implementation of inventive concepts. Ovals (FIG. 5A) and rectangles (5B and 5C) can be used to create like-shaped domains on the scaffold. For example, in the embodiment shown, the ovals (A) can be used to create cell seeding domains at two distinct locations on the scaffold. Rectangles (B and C) can be used to create conduits for cellular growth and differentiation away from the cell seeding domains. For example, conduits B and C can include a cell attachment factor such as PDL, which can encourage neuronal growth from the cell seeding domains to an intersection, and the cells of the distinct cell seeding domain can communicate with each other. Such communication can be via synapses that are formed at the intersection of the conduits (in FIG. 5, the intersection of the rectangles). Alternatively, cells can extend along the conduits and eventually form synapses with cells from the other cell seeding domain at a location that is within a conduit but outside of the conduit intersection (for example, if cells extend past the intersection and proceed further down the conduit, forming synapses at a location that is past the intersection).

Figure 10:
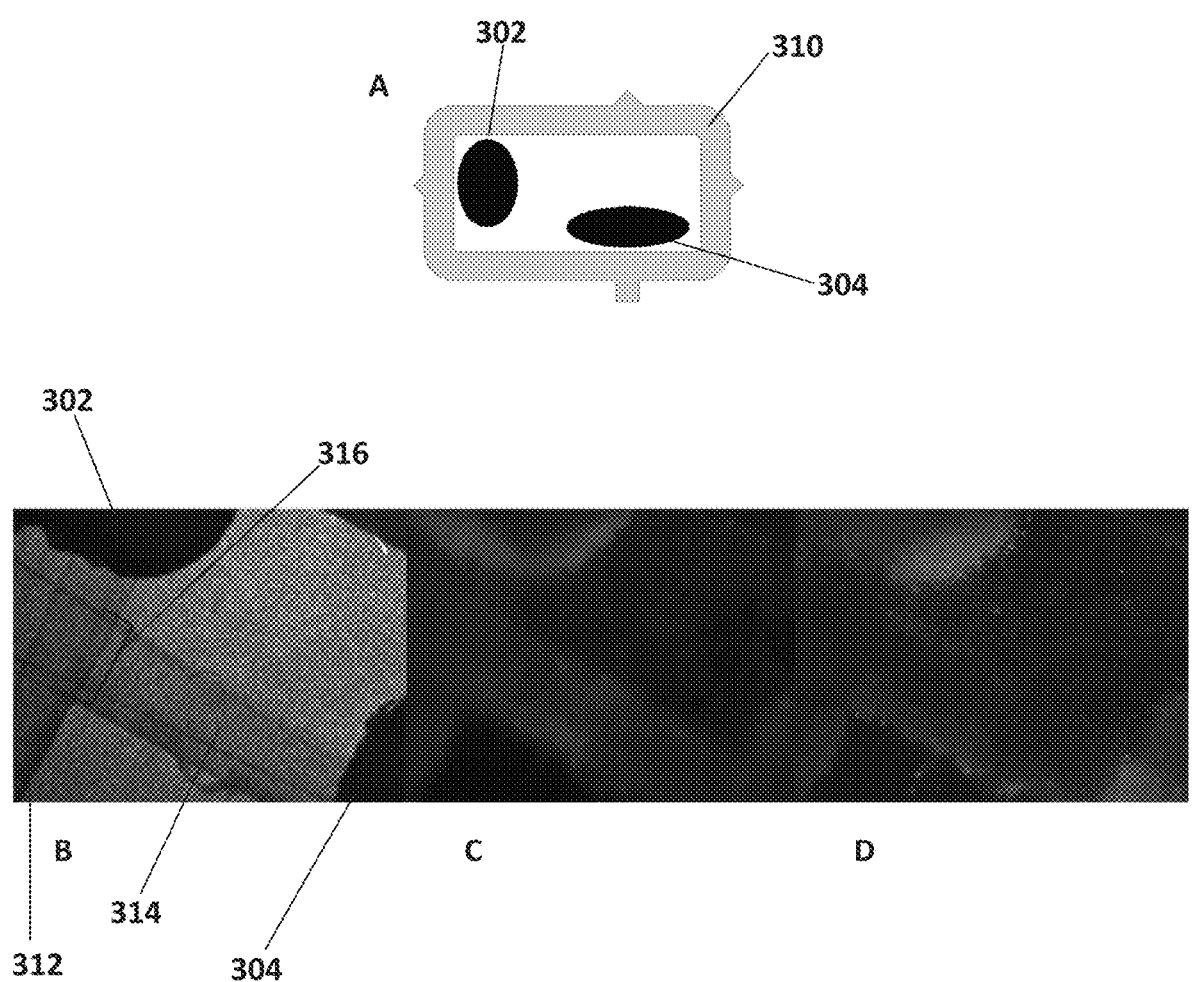
FIG. 10A is a schematic representation of an illustrative bioartificial open-field electrophysiology tissue scaffold, modeled after the rat hippocampal CA3-CA1 Schaffer-collateral pathway. Aligned nanofibers are deposited vertically and horizontally between the markings on the scaffold frame, and annealed.
FIGS. 10B-10D are Brightfield and fluorescence images (C, calcein; D, Retrobeads®) of resulting bioartificial tissue after 10 weeks in culture (25× magnification).

A further implementation is shown in FIG. 10A. As discussed in Example 9, photoreactive nanofiber cylinders and were prepared and processed with PDL, followed by further processing into 2 mm and 3 mm diameter cylinders using a circular die cutter. The small disc-shaped cylinders (~200 microns thick) were seeded with hippocampal cultures on both sides and then placed on the surface of a nanofibrous scaffold. The cylinders thus defined cell culture domains 302 and 304 shown in FIG. 10.

FIG. 10A is a schematic representation of bioartificial open-field electrophysiology tissue scaffold, modeled after the rat hippocampal CA3-CA1 Schaffer-collateral pathway, showing the frame assembly 310 and location of cultured neuronal/glial cell populations 302 and 304. FIGS. 10B-D also show aligned nanofibrous conduits 312 and 314 that contact each cell culture domain 302 and 304 and contact each other at an intersection 316 that is located outside both cell culture domains.

Various reagents compatible with cell growth may be used. Examples of such reagents include polyethylene glycol (PEG), used to prevent or inhibit cell attachment and growth whereas poly D-lysine (PDL), used to incite or encourage cells to attach and grow.

In some implementations, alternating patterns of cell seeding domains and passivating polymer can be provided by 3-D printing technology. 3-D printing (additive manufacturing) is a process of making a three-dimensional solid object of virtually any shape from a digital model. 3D printing is achieved using an additive process, where successive layers of material are laid down in different shapes. This technology uses special printers for solid object creation. The 3-D printers jet materials one layer at a time, enabling the fabrication of fully printed prototypes. The scaffolds can provide 3-D cell culture for the development of simple tissue constructs. More complex scaffolds using 3-D printing can assist development of more complex structures essential for biofunctional tissues. An exemplary material that is useful for 3-D printing or additive manufacturing are hydrogels since they embody tissue-like flexibility while possessing viscoelastic properties, interstitial flow and diffusive transport characteristics similar to native tissues. Various natural polymers used to form hydrogels, such as fibrinogen, hyaluronic acid (HA), collagen, alginate, gelatin and chitosan are useful in the invention. Additionally synthetic polymers such PEG and PEG derivatives, PLA and PVA are useful in the invention.

In some aspects, passivating polymer can be applied to the scaffold in combination with photolithographic masks or by printing. In one embodiment, the use of fibers, such as microfibers or nanofibers, with latent reactive groups, such as photoreactive moieties, for the simultaneous patterning of surface chemistry and control over nanoscale topography to direct in vitro neural ontogeny has been found to provide surprising benefits.

In another embodiment, the design of the scaffold, such as a neural scaffold, is optimized for extracellular field recording techniques. This novel combination of random nonwoven and aligned nanofiber topography with surface chemistry, such as photo-patterned surface chemistry, provides the necessary features for the development of a bioartificial brain slice, patterned to generate open field potentials for use in electrophysiological assays.

Additional embodiments of the invention provide a device for electrophysiological screening, the device comprising: (a) a nanofibrous scaffold; (b) at least first and second cell seeding domains; and (c) at least first and second nanofibrous conduits arranged on the scaffold, wherein the first conduit is in contact with the first cell seeding domain, and the second conduit is in contact with the second cell seeding domain, wherein the first conduit and the second conduit contact each other at an intersection, and wherein the first and second cell seeding domains, and the first and second nanofibrous conduits do not contact each other outside the intersection.

In still further aspects, bioartificial brain slice scaffolds are prepared from synthetic photoreactive nanofibers, which can be mass produced at low cost. For example Human Neural Progenitor (hNP) cell lines can be directed to differentiate into multiple neuronal phenotypes and are already serving as model systems for the study of neurological diseases and disorders. The 3-dimensional scaffolds direct the growth of neuronal co-cultures derived from existing cell lines into in vivo-like neural circuits, allowing high volumes of brain slices, preferably populated with human cells, to be produced by the end user. Glia can also be included in the scaffold co-cultures to maintain, modulate, and improve neuronal survival and function, and may also serve as targets in drug discovery or drug testing. The bioartificial brain slice scaffold can be provided in a standardized format that is compatible with common electrophysiological equipment.

Inventive scaffolds can be utilized as a platform to study processes in electrophysiology and can be used to evaluate therapies as an intermediate decision-making step in high throughput screening of drugs. Generally speaking, inventive scaffolds are seeded with electrically excitable cells, and the cells are cultured on the scaffold. After sufficient time for cells to form a network, the scaffold is connected to a stimulating electrode. A baseline open field potential is established. Thereafter, a putative drug is applied to the scaffold, and change in the open field potential is monitored.

Accordingly, provided herein are methods for screening pharmaceuticals for treatment efficacy using the 3D scaffold composites. In these methods, the scaffold composites are seeded with excitable cells, cells are allowed to grow and form a functional synaptic circuit, and pharmaceuticals are administered to the cells in the scaffold composite for a period of time. The scaffold is then subjected to open field potential measurements.

Open field excitatory/inhibitory post-synaptic potentials (fEPSP, fIPSP) measure the ensemble synaptic activity of neurons in open field circuits, as opposed to action potentials or unit activity such as spikes and bursts. Open field potentials can also measure presynaptic and postsynaptic ensemble action potentials (pre synaptic fiber volley and post synaptic pop-spike (population spike), respectively, but to measure EPSP or IPSP for drug screening one needs to use patch clamp methodology (the exception, as mentioned above, being organotypic brain slice culture).

It is contemplated that the invention can be provided as kits as well as systems for use in electrophysiological drug and disease screening. In one embodiment the scaffolds may be provided with instructions for use. In another embodiment a system comprising scaffolds and electrophysiological equipment may be provided.

In still further implementations, inventive concepts provide methods to generate a cell culture scaffolds that can impart open field architecture to nascent electrically excitable tissues derived from suspension cells. The cell culture scaffold containing open field architecture includes at least 1) a support, and 2) guidance cues for developing circuits (neurites, axons, dendrites). The guidance cues are arranged to generate circuit-level tissue architecture necessary to achieve open field dipoles in electrically active tissues composed of many excitable cells. Guidance cues can be generated using a variety of methods including 3D printing, microcontact printing, ablation or etching of scaffold materials, deposition of carbon nanotubes, and the like. Additionally, a suitable support material may comprise any of a large variety non-cytotoxic solids and gels. Illustrative support material includes, but is not limited to, silicones, polyolefins, vinyl polymers, polystyrenes, polyacrylates, poly methacrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, phenolics, amino-epoxy resins, polyesters, polyethers, cellulose-based plastics, rubber-like plastics, copolymers, or any mixtures or combinations thereof. Other suitable support materials include silica glass, alginate, collagen, various hydrogels, self-assembled nanofibers, proteins, nucleic acids, polysaccharides, drawn or spun nanofibers, synthetic extracellular matrix, animal and plant extracts, and the like.

An additional level of tissue patterning can be provided through the use of cell attachment or repulsive regions in the scaffold, to influence the location of glia and neuronal soma in the developing tissue. Alternatively, a cell printer, magnetism (cells can be magnetically labeled), electrostatics, or a variety of mechanical methods could be used to pattern the location of cells when seeding the scaffold, such as seeding with the assistance of micromanipulation techniques, or seeding the scaffold with small cell sheets, spheroids, or tissue chunks. Finally, the use of immobilized growth factors on the scaffold is expected to provide an additional level of control over cellular plasticity and tissue development of bioartificial tissues.

Inventive concepts will now be described with reference to the following non-limiting Examples.

EXAMPLES

In the following examples, all percentages are by weight, unless specified otherwise. Morphology of all nanofibers and nanofibrous scaffolds was investigated using a Hitachi S-3500N SEM. Samples were mounted on an aluminum stub using carbon tape and gold sputter-coated before viewing. Pore size was determined visually by scanning electron microscope (SEM) analysis. Pore size was determined as an average of a minimum of 40 pores at different points within the nanofiber or nanofibrous scaffold.

The trifunctional triazine crosslinker (the "Photoreactive Crosslinker") used in the Examples was prepared as described in Example 1 of U.S. Patent Application Publication No. US 2014/0294783 A1 (Jie Wen et al., published 2 Oct. 2014).

Example 1

Electrospinning of Random-Nonwoven and Aligned Photoreactive Nanofibers

Photoreactive polycaprolactone nanofibers were prepared by electrospinning solutions containing 10% poly($\varepsilon$-caprolactone) (PCL, with an average molecular weight of 80 kDa, purchased from Sigma-Aldrich) and 0.1% Photoreactive Crosslinker in a 1:1 solution of tetrahydrofuran:N,N-dimethylformamide. Electrospinning procedure was as described in Example 2 of U.S. Patent Application Publication No. US 2014/0294783 A1 (Jie Wen et al., published 2 Oct. 2014). Random, nonwoven nanofiber mats (meshes) were collected as described in the referenced Example.

Figure 3:
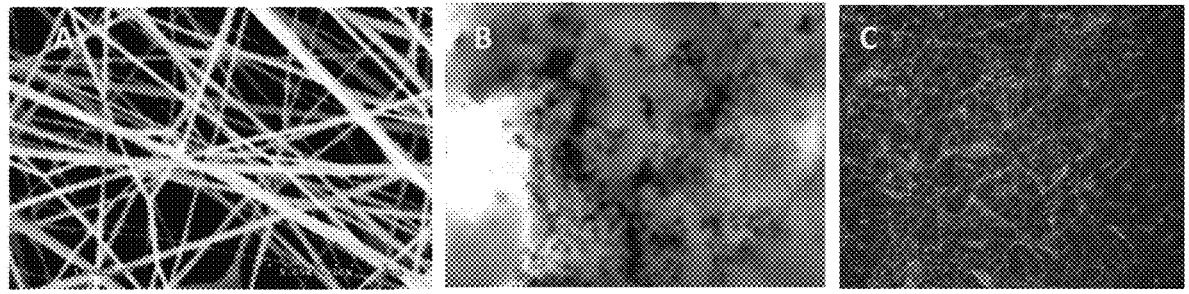
FIG. 3 shows electron micrographs of photoreactive PCL nanofibers (FIG. 3A); C2C12 cells growing on 3-dimensional scaffolds (FIG. 3B); and BAE cells grown on nanofiber mats (FIG. 3C).

The formed nanofiber mats were removed, placed in a vacuum chamber for at least 48 hours to remove organic solvent residue, then stored in a desiccator. Fiber diameter, morphology and pore size of the dried nanofibers were characterized using light and scanning electron microscopy (SEM). FIG. 3A illustrates an SEM image of PCL nanofibers containing 1% Photoreactive Crosslinker, by dry weight. Diameter of the nanofibers was 200 nm to 300 nm. Pore size was 1-10 µm.

To allow for cellular penetration of random nonwoven nanofiber mats in a cell culture scaffold, a pore size of approximately 5 microns or greater can be desirable. Aligned fiber diameter on the order of 200-400 nm can be beneficial for axon and neurite guidance.

Average mat thickness was measured using frozen mats and a microcaliper. Mat thickness was controlled by varying the duration of spinning. Target mat thickness of random nonwoven mats was 125 microns for random nonwoven mats (actual thickness was 141 microns), and 50 microns for the aligned nanofiber mats.

Example 2

Photopatterning of Nanofiber Mats

Nanofiber mats were treated to create a surface that included a passivating polymer (PEG) surrounding discrete domains for cell culture and growth. Silver halide photolithographic masks were used to create the discrete cell culture domains.

Work was performed using sterile procedures. Materials were sterilized with 70% ethanol and illuminated with UV light (306 nm) for 3 minutes per side. Prior to photopatterning, photoreactive nanofiber mats were incubated in a solution of polyethylene glycol (PEG, MW 10K, Sigma) for 2 hours, and dried in the dark.

Complimentary silver halide photolithographic films (CAD/Art Services, Inc., Bandon, Oreg.) were used to conjugate polyethylene glycol (PEG) outside of the desired cell growth and attachment areas (see FIG. 5 and FIG. 1B). The mask sets were provided in oval shapes. Complementary masks enabled simultaneous light exposure to both sides of the nanofiber mat and ensure mask alignment and optimal light penetration. The random nonwoven nanofiber mats were trimmed with a scalpel blade at the edge of their masks (5×9 mm masks, produced a 1 mm overhang for subsequent annealing, resulting in a 4×8 mm nanofiber scaffold, see FIGS. 1 and 2).

The masks (ovals) were used for the random nanofiber mats to provide a delimited area for cell body attachment and ingrowth (FIG. 5). The nanofiber mats were sandwiched between the complimentary photomasks and UV irradiation was then applied for a period of 3 minutes per side. Illumination conditions permitted the photoreactive groups contained in the nanofibers to form covalent bonds with the PEG, thereby immobilizing the passivating polymer at areas outside the masks Following photopatterning, photolithographic masks were removed, and the nanofiber mats were rinsed well with cell culture grade water and incubated briefly in a poly-D-Lysine solution (PDL, MW 175K, Sigma). PDL promotes cell attachment and neurite outgrowth. The mats were then removed from PDL solution, dried, and re-exposed to UV light without the masks for a period of 3 minutes per side. Because PEG is a well-known biological passivator, the polymer was used to prevent non-specific adsorption of PDL outside of the oval areas created by the photolithographic masks. The resulting photopatterned nanofiber mats thus contained discrete domains of PDL (oval shaped) to promote cell attachment and neurite growth, surrounded by passivated regions of PEG.

Aligned nanofibers promoted neurite outgrowth and guided axons to the target neuropil. Aligned nanofibers were collected on to the parallel plate collector and misted with PDL solution until saturated. After drying in the dark, the fiber were collected directly onto patterned or unpatterned random nonwoven nanofiber mats, annealed, and cured with UV light as above for 3 minutes from the top. The annealed scaffolds were then rinsed with sterile water in a tissue culture hood and dried.

Results indicated that neurons and neurites strongly preferred to grow on the PDL coated areas as compared to the PEG surface (data not shown here; see also Examples 9 and 10; FIGS. 7F and 7G).

Example 3

Cytocompatibility of Scaffolding Material

To investigate the ability of prepared scaffolding material to support cell adhesion and proliferation, samples were sterilized with 70% ethanol for 24 hours, washed extensively with PBS (0.1M, pH 7.4) and exposed to UV light for 40 minutes (CL 1000 ultraviolet crosslinker, UVP). Scaffold materials were seeded with myoblasts (C2C12 cells, ATCC), endothelial cells (BAEC (Bovine aortic endothelial cells), Lonza Biosciences), and neural cells to observe the ability of the nanofibrous scaffolds to support growth of these cells.

Muscle myoblast cells. FIG. 3B shows attachment and growth of C2C12 cells on nanofibrous scaffolds. The scaffolds were prepared as described in Example 1. An amount of the formed nanofibrous mesh was immersed in 20 ml of 50 mg/ml PAA aqueous solution for 30 minutes in a quartz round dish (Quartz Scientific, Inc., Fairport Harbor, Ohio). Mild agitation was applied to remove the air bubbles trapped in the nanofibers. Two minutes of UV irradiation was then applied to the mixture using a UVM400 ultraviolet lamp (Harland Medical, Eden Prairie, Minn., distance from the light source was 8 inches). The nanofiber mesh was flipped over and UV illumination applied again. The coated nanofiber meshes were rinsed with distilled water three times and washed overnight. The functionalized nanofibers (which now contained carboxy reactive groups) were then lyophilized. BMP-2 was immobilized on the carboxy-functionalized nanofibers through an EDC/NHS coupling method. Carboxylated nanofiber meshes were immersed in a fresh solution containing 10 mg/ml EDC and 5 mg/ml NHS, in water, adjusted to pH 4.5, After incubation on a shaker (100 rpm) at 4° C. for 30 minutes, the activated samples were removed, rinsed quickly with ice cold water, and immediately immersed in protein solution (5.0 µg/ml, PBS, pH 7.4). After gentle agitation at room temperature for two hours, the nanofibers were removed and rinsed with PBS.

C2C12 cells were purchased from ATCC and were seeded and maintained in DMEM (Sigma Chemical Co., St. Louis, Mo.) containing 15% FBS (Gibco, Grand Island, N.Y.) and antibiotics (100 U/ml of penicillin-G and 100 µg/ml of streptomycin) at 37° C. in a humidified atmosphere of 5% $CO_2$ in air.

Prior to cell seeding, the scaffolds were preconditioned with growth media for 2 hours. C2C12 cells were seeded onto the scaffolds (50,000 cells/m, 2 ml in 6-well plates). After 5 days in culture, fixed sections were embedded in paraffin and 10 micron thick sections were cut. Sections taken from the scaffold were stained with Hematoxylin and Eosin solutions (NovaUltra™ H&E Stain kit). Sections were viewed and photographed using Leica microscope and imaging software. Cells attached and spread on nanofibrous scaffolds as illustrated in FIG. 3B. FIG. 3B shows C2C12 cells growing throughout the scaffold material. The cells were not only localized at the top section of the scaffold but had also penetrated at least 70-80 micron deep inside the scaffolds. The light microscope image of FIG. 3B shows cell penetration in the central part of the scaffold at 70 micron depth.

Endothelial cells. FIG. 3C shows RAE cells grown on photoreactive PCL nanofiber mats and stained with phalloidin. Nanofiber mats were seeded with bovine aortic endothelial cells (BAF, Gibco) to observe the ability of the nanofibers to support growth and differentiation of these cells. Cell seeding was at a density of 30,000 cells per mat. The cells were cultured in DMEM+10% FBS media (Life Technologies, Inc.) for a period of four days, at 37° C. in a humidified atmosphere of 5% $CO_2$. After four days, the cells were fixed with 3.7% formaldehyde for ten minutes at room temperature. The cells were then permeabilized with 0.1% Triton in PBS for 5 minutes at room temperature, washed with PBS and then 1:500 dilution of Phalloidin-Texas red (Life Technologies, Inc.) was added for a period of at least 30 minutes. After three rinses with PBS, the stained cultures were observed under an inverted microscope. The healthy and intact cytoskeletal actin network indicated normal growth and proliferation.

Neural cells. P0-5 rat hippocampi were digested with papain and triturated. The suspension of hippocampal cells was concentrated by centrifugation and seeded into the wells containing random nanofiber mats (300,000 cells/well, mats produced as described in Example 2), saturated with cell culture media (Neurobasal+B27+Glutamax™+10% horse serum) in 24-well Ultra-Low Attachment Surface plates (Corning). Cells were grown in a humidified $CO_2$ incubator with 5% $CO_2$ at 37° C. Two hours were allotted fur cell adherence prior to submerging the mats into media.

After two weeks in culture, cytotoxicity was measured with the live/dead assay (Life Technologies) according to the manufacturer's protocol. Cells cultured on standard polylysine coated TCPS plates were used as control (not shown). Formulations with at least 90% cell survival were considered non-cytotoxic. As shown in FIGS. 7F and 7G, the vast majority of cells were stained with only green and not red, indicating that they were alive and healthy.

The proliferation of glial cells on the nanofiber mats can be determined at intervals, such as after 1, 7, and 21 days.

Figure 4:
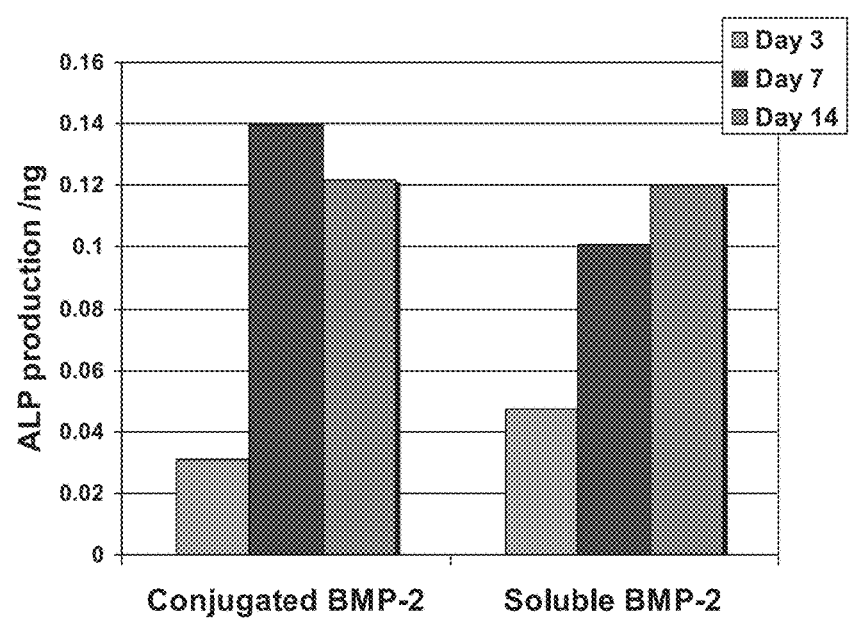
FIG. 4 is a graph showing that the biological activity of a growth factor is preserved when conjugated to photoreactive nanofiber scaffolds.

FIG. 4 illustrates bioactivity of a growth factor immobilized onto the scaffold material. Carboxy-modified nanofibers were prepared as described above.

To assess the bioactivity of immobilized BMP-2, alkaline phosphatase (ALP) activity on mesenchymal stem cells seeded on the conjugated scaffolds and on control scaffolds with soluble BMP-2 (500 ng/ml) was determined for day 3, day 7 and day 14 of cell culture.

The cells were cultured at 37° C. in a humidified atmosphere of 5% $CO_2$ in DMEM+15% FBS medium (GIBCO, Grand Island, N.Y.).

Prior to cell seeding, scaffolds were sterilized by UV irradiation for 30 seconds per side using a Harland Medical UV system, and pre-wetted for 24 hours in Hanks' Balanced Salt Solution (HBSS; BioSource International, Camarillo, Calif.).

Scaffolds were then placed in 24-well tissue culture plates (Corning Glass Works, Corning, N.Y.). Cell suspension was seeded into the scaffolds in 200,000 cells, 1.5 mL volume. Equal numbers of cells were seeded onto nanofibrous scaffolds.

Cells were lysed with 2 ml of extraction reagent (Sigma-Aldrich), and 50 µl of the cell extract and ALP standard solutions were incubated with 100 µl of p-nitrophenyl phosphate solution at room temperature for one hour. The p-nitrophenol production was measured at 405 nm. ALP expression was calculated based on a standard curve.

Results showed overall, conjugated BMP-2 retained activity at similar levels to soluble protein. Thus, biologically active materials can be conjugated to the nanofiber and retain their activity.

Example 4

Assembly of Photopatterned Mats into Scaffolds Containing Architecture for Open Field Generation Photopatterned nanofiber mats prepared as described in Example 2 herein were rinsed extensively in sterile endotoxin-free water to remove unbound PDL, and dried prior to lamination. Nanofiber mats were then stacked in the following order: random nonwoven, horizontal aligned, vertical aligned, random nonwoven. The vertical aligned mat (FIG. 2C) was placed on the right end of the stack (see FIG. 2).

The total scaffold thickness was approximately 350 microns, which is the thickness of brain slices commonly used for electrophysiology. The 1 mm overhanging edges of the scaffold stack were then annealed by heating to >60° C. with a sterile die (rectangular, inner dimensions 4×8mm). Scaffold thickness and architecture were adjusted as needed.

Example 5

Electrophysiological and Pharmacological Testing of Bioartificial Hippocampal Brain Slice Dissociated hippocampal cells were seeded onto annealed scaffolds containing photopatterned random and aligned mats prepared as described in Examples 2 and 4 herein (see FIGS. 2 and 5). Cells were seeded onto both oval PDL regions of the annealed scaffolds, using the procedure described in Example 3 herein. The two oval regions connected by perpendicular aligned fibers represented a co-culture system for innervation between two physically separate cell populations. In this example, the neural circuitry was modeled after the rat hippocampal CA3-CA1 Schaffer Collateral pathway. After the initial 2-hour time for cell adherence, scaffolds were turned over and the oval regions on the other side were reseeded. After 2 additional hours, scaffolds were submerged in growth media. The formation of functional chemical synapses between the co-cultures, along the parallel nanofiber tracts, was expected to occur in approximately 10 days.

Bioartificial slices were removed from the incubator for electrophysiological testing at 10, 14, and 21 days in vitro (d.i.v.). For electrophysiological field recordings, bioartificial slices were suspended on a nylon mesh in a small (350-400 µl) recording chamber and perfused with artificial cerebrospinal fluid (ACSF) at a rate of 2.5-3 ml/min (submerged mode). The temperature in the recording chamber was held at 30-32° C.

FIG. 6 shows a schematic diagram of the electrophysiological field recordings. Recordings were made using an ACSF-filled glass micropipette 22.0 (2-4 MΩ) positioned as illustrated in FIG. 6 and connected via a head stage to the amplifier. Signals were digitized at 100 kHz using a Digidata 1550 series interface (Axon Instruments) running Clampex. Synaptic responses were evoked by electrical stimulation using a bipolar tungsten electrode 210 (tip spacing, 140 µm; Frederick Haer Company) and a 100 µs square wave test pulse was delivered at 60 second intervals (FIG. 6). Chemical synapses are represented at 230 in FIG. 6.

Stimulus-response relationship was established over the range of 0-1000 microV. The stimulation intensity was then adjusted to produce a basal response that was 25-30% of the maximum field EPSP amplitude.

This example describes a means to test the ability of bioartificial open field scaffolds to support the ontogeny of an excitatory synaptic circuit, modeled after the hippocampal CA3-CA1 pathway, for extracellular field recording assays (e.g. monitoring fEPSPs, pop-spikes, and/or fEPSPs). Additionally, the bioartificial brain slices can be used to monitor physiological properties of the synaptic network, which includes both neurons and glia, as a means of testing or screening the effects of pharmaceuticals, biologics, gene therapeutics, and the like, on neural network activity and plasticity. In one preferred embodiment, the bioartificial brain slice can be seeded with human neurons and glia or their progenitor cells.

Example 6

Photopatterning of Nanofiber Scaffolds with Cell-Modulatory Materials

In this example, cell attachment (as well as subsequent growth and spreading) was modulated through photopatterning cell attachment and passivation factors. Photoreactive nanofibers shown in FIG. 7A-G were prepared by electrospinning a solution of 20% (w/v) polycaprolactone (PCL, 150 kDa, Scientific Polymer Products) and 0.2% (w/v) of the Photoreactive Crosslinker, from 2,2,2-Trifluoroethanol (TFE, Sigma Aldrich). Electrospinning was performed as described in Example 1 herein. Nanofibers were collected at ~40% relative humidity onto a 3×4 inch grounded aluminum collector plate positioned 17 cm from the syringe needle (27 awg, blunt). A voltage of 15 kV was applied to the syringe needle and a syringe pump was used to provide a constant flow rate of 0.2 mL/hr. A variety of parameters were tested within the range shown in Table 1.

TABLE 1

|  | [Polymer] (% W/V) | [Dopant] (% w/v) | Flow (mL/hr) | E.P. (kV) | h (cm) | Needle |
| --- | --- | --- | --- | --- | --- | --- |
| Upper | 20 | 0 | 1.4 | 15 | 20 | 22 G |
| Optimal | 20 | 0 | 0.2 | 15 | 17 | 27 G |
| Lower | 20 | 0 | 0.2 | 3.75 | 5 | 27 G |

*Mat thickness tuned by duration.
**[Photoreactive Crosslinker]/[Polymer] = 0.01

After drying under ambient conditions for a minimum of 24 hours in the dark, photoreactive nanofiber mats were processed with polyethylene glycol (PEG, 4800 g/mol Sigma Aldrich) 2 g/L and/or poly-D-Lysine (PDL, 70-150 kD, Sigma Aldrich) 0.5 g/L borate buffer, pH 8.5, and using custom photomasks obtained from CAD/Art Services, Inc. Photoreactive nanofiber mats were cured using ultraviolet light (Ushio UVB bulbs #G15T8E) for two minutes per side at a distance of 5 cm. Nanofiber mats were rinsed with PBS 3 times after each UV-curing step. A final rinse in cell culture grade water was used to remove salts after processing.

For cell culture, hippocampi were harvested from P0-P3 Sprague Dawley (SD) rats using procedures reviewed and approved by the University of Minnesota IACUC. After cell dissociation, cells were grown in Neurohasal A Media (Invitrogen) supplemented with B-27 (Gibco), Glutamax (Gibco), and 10% heat-inactivated horse serum (Gibco). Random nonwoven nanofiber mat scaffolds were seeded in 24-well Low-Cell-Binding plates (Nunc) at 300,000 cells per well. After 3 hours, the media was exchanged to remove the remaining cell suspension. Cultures were maintained at 5% $CO_2$, 37° C. for up to 12 weeks.

Figure 7:
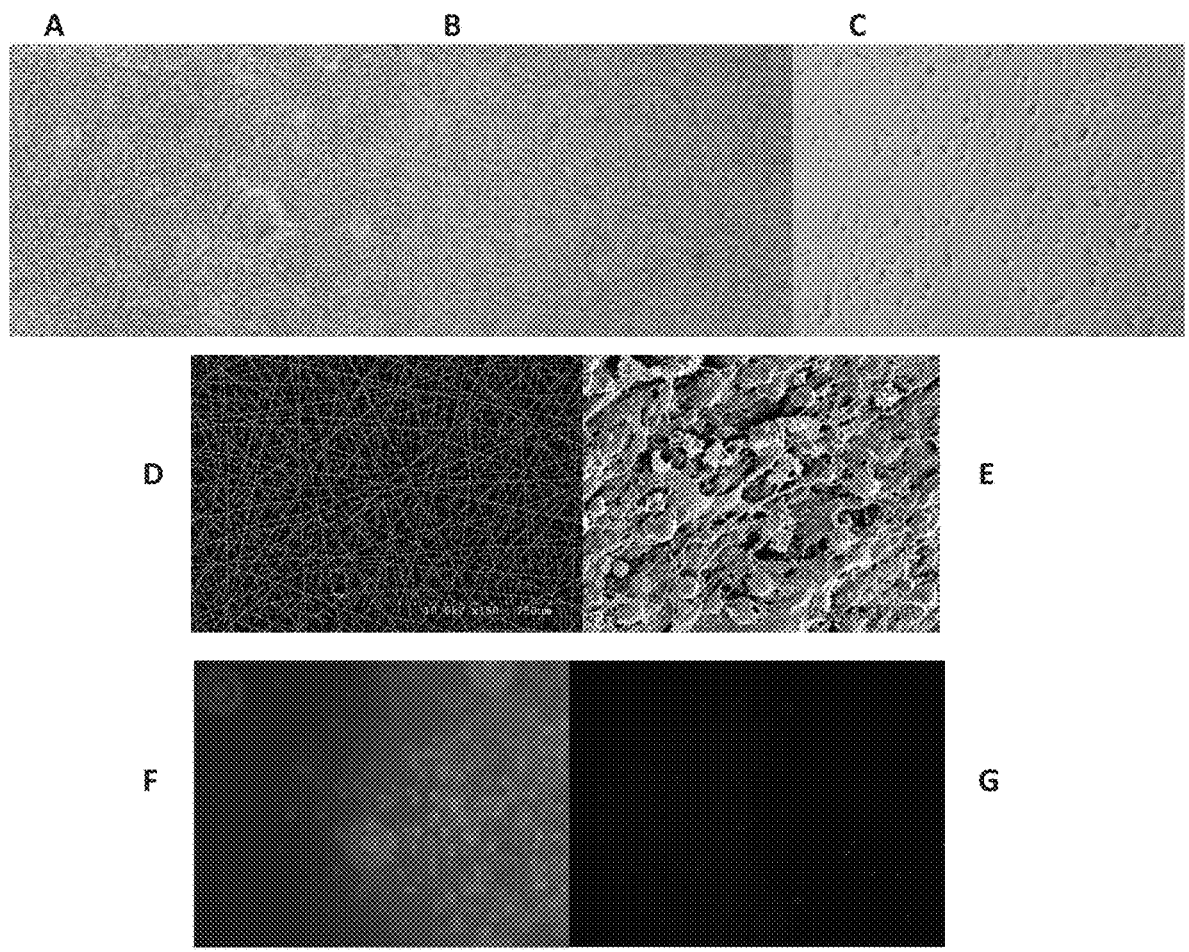
FIG. 7 shows Brightfield images of hippocampal cultures grown on non-woven mat nanofiber scaffolds (A, with PEG photoconjugation; B, with PDL photoconjugation; C, TCPS control) at 100× magnification.

Photomicrographs of hippocampal cultures (14 d.i.v.) grown on photoreactive PCL random nonwoven nanofiber mat scaffolds (see optimal conditions above) that were photoconjugated with PEG (FIG. 7A), PDL (FIG. 7B), or photopatterned with both PEG and PDL (FIGS. 7F-7G) to modify the nanofiber surface, or on standard TCPS (FIG. 7C, control), are shown in FIG. 7.

As seen in FIG. 7A, cells clumped up and formed spheres above the passivating PEG-surface, whereas in FIG. 7B cells attached, spread, and infiltrated the nanofiber scaffold where modified with attachment promoting PDL-surface. A control surface of flat tissue culture polystyrene (TCPS, Nunclon Delta, Nunc) is shown for comparison in FIG. 7C. Also shown in FIG. 7 are SEM images of scaffolds with and without hippocampal cultures. Average nanofiber diameter was 1.245+/−0.114 microns (1 S.D.), and the pore size was estimated to be approximately 10 microns. In FIG. 7F, fluorescently stained cells (green, calcein staining) can be seen clustering primarily on the PDL photopatterned region, and not on the surrounding PEG-passivated region.

Example 7

Use of Aligned Photoreactive Nanofibers to Guide Neurite Extension

Electrospun aligned photoreactive nanofibers were processed with PDL to generate a topographical neurite guidance scaffold. The aligned fibers were used to control neurite extension and generate a spatially-controlled innervation pattern between two or more cell populations on or within a cell culture scaffold. The photopatterning of photoreactive nanofiber scaffolds with various biomolecules, growth factors, or biomaterials, can be used as an architectural element to control the cellular attachment (from a cell suspension), growth, migration, proliferation, and/or differentiation of cell populations, as well as neurite, axon, or dendritic guidance cues, such as growth factor gradients or extension promoting substances (e.g. collagen), in a cell culture scaffold system. This architectural element of a cell culture scaffold is instrumental for ontogenic control of bioartificial tissues designed for compatibility with open field potential generation, such as is employed in electrophysiological assays of some native neural tissues (such as hippocampus).

Aligned fibers were prepared according to the method of Secasanu et. al. (Biotechnol. Prog. 25(4):1169-1175, July-August 2009), which uses deposition target geometry to influence the electric field geometry in such a way as to efficiently and reproducibly generate uniaxially aligned fibers on a solid state collector. As in Example 6, a variety of polymers, polymer concentrations, solvents, mixed solvents, electric field strengths, flow rates, and collector distances were tested, as well as the concentration of Photoreactive Crosslinker. The inclusion of volatile and non-volatile surfactants, amphiphiles, and salts in the electrospinning solutions to modify photoreactive nanofiber morphology were also investigated.

TABLE 2

|  | [Polymer] (% W/V) | [Dopant] (% w/v) | Flow (mL/hr) | E.P. (kV) | h (cm) |
|---|---|---|---|---|---|
| Upper | 10 | 0.2 | 0.25 | 25 | 25 |
| Optimal | 13% PCL in TFE | 0.2% Na Acetate | 0.15 | 20 | 20 |
| Lower | 13 | 0 | 0.06 | 14 | 14 |

*Solutions include 13% PCL in TFE, 10% Nylon6,6 in TCE, 10% Nylon6,6 in TCE/TFE, 13% PCL in Chloroform, 13% PCL in Chloroform/TFE
**[ISurLite]/[Polymer] = 0.01 (wt./wt. %)
***All trials used a 27 Gauge needle PCL nanofibers having a diameter of approximately 200 nm to 400 nm were generated as follows. A solution of 13% (w/v) polycaprolactone (PCL, 150 kDa, Scientific Polymer Products), 0.2% (w/v) sodium acetate (Sigma Aldrich) and 0.13% (w/v) Photoreactive Crosslinker, in 2,2,2-Trifluoroethanol (TFE, Sigma Aldrich) was prepared. The solution was placed into a 27 gauge blunt needed (27 awg), a voltage of 20 kV was applied to the syringe needle and a syringe pump was used to provide a constant flow rate of 0.15 mL/hour. Fibers were collected at ~40% relative humidity onto a Secasanu-type grounded aluminum collector plate, positioned 21 cm from the syringe needle, After drying under ambient conditions for a minimum of 24 hours in the dark, uniaxially aligned photoreactive nanofiber mats were collected with PCL/Photoreactive Crosslinker coated round glass coverslips (12CIR-1D, Fisher Scientific) and then immersed in a solution of poly-D-Lysine (PDL, 70-150 kD, Sigma Aldrich) in 0.5 g/L in borate buffer, pH 8.5. These uniaxially aligned nanofiber discs were then cured using ultraviolet light (Ushio UVB bulbs #G15T8E) for two minutes at a distance of 5 cm. The PDL-modified discs were rinsed with PBS 3 times after the UV-curing step. A final rinse in cell culture grade water was used to remove salts after processing.

For cell culture, hippocampi were harvested from P0-P3 Sprague Dawley (SD) rats using procedures reviewed and approved by the University of Minnesota IACUC. After cell dissociation, cells were grown in Neurobasal A Media (Invitrogen) supplemented with B-27 (Gibco), Glutamax (Gibco), and 10% heat-inactivated horse serum (Gibco). Cells were seeded in 24-well plates (TCPS, Nunclon Delta, Nunc) on PDL-modified discs at 75,000 cells per well. After 3 hours, the media was exchanged to remove any remaining cells in suspension. Cultures were maintained at 5% $CO_2$, 37° C. for up to 4 weeks.

Figure 8:
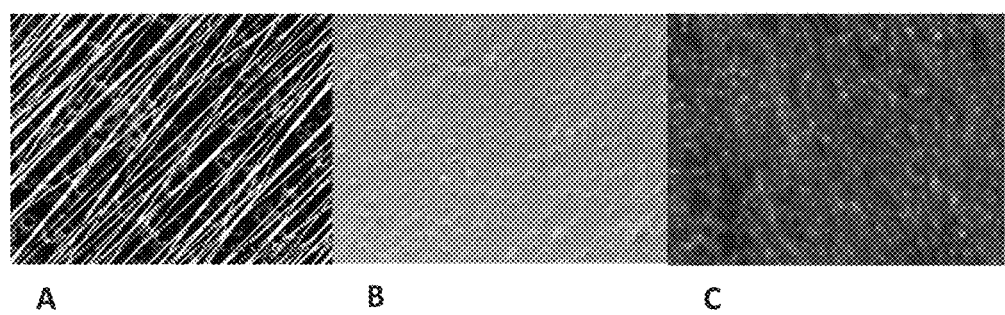
FIG. 8 shows images of aligned nanofibers with photoimmobilized PDL surface on PCL-coated coverslips (8A, SEM, scale bar 20 microns); as well as Brightfield (8B) and fluorescent (8C) images of hippocampal cultures grown on the aligned nanofibers on PCL-coated coverslips. The nanofibers and the PCL coating included photoimmobilized PDL surface to promote cell attachment and extension of aligned neurites.

Electron micrograph of PDL-modified uniaxially aligned photoreactive nanofiber coated discs are shown in FIG. 8a. Photomicrograph of hippocampal cultures (14 d.i.v.) grown on these discs are shown in FIG. 8b. In FIG. 8c, cultures were stained with calcein (Invitrogen, according to manufacturer's protocol) to better reveal cell morphology. As seen in FIG. 8a, nanofiber alignment was good (scale bar 20 microns). Average nanofiber diameter in this example was 241+/−0.031 nm. In FIGS. 8b and 8c, cell morphology and particularly neurite extension is substantially aligned with the underlying nanofiber topography.

Example 8

Mechanical Patterning of Nanofiber Scaffolds

The mechanical patterning of tissue scaffolds with pre-seeded or non pre-seeded scaffold components can be used as an architectural element to control the cellular placement, growth, migration, proliferation, and/or differentiation of cell populations in a cell culture scaffold system. This architectural element of a cell culture scaffold is instrumental for ontogenic control of bioartificial tissues designed to support open field potential generation for use in electrophysiological assays.

Figure 9:
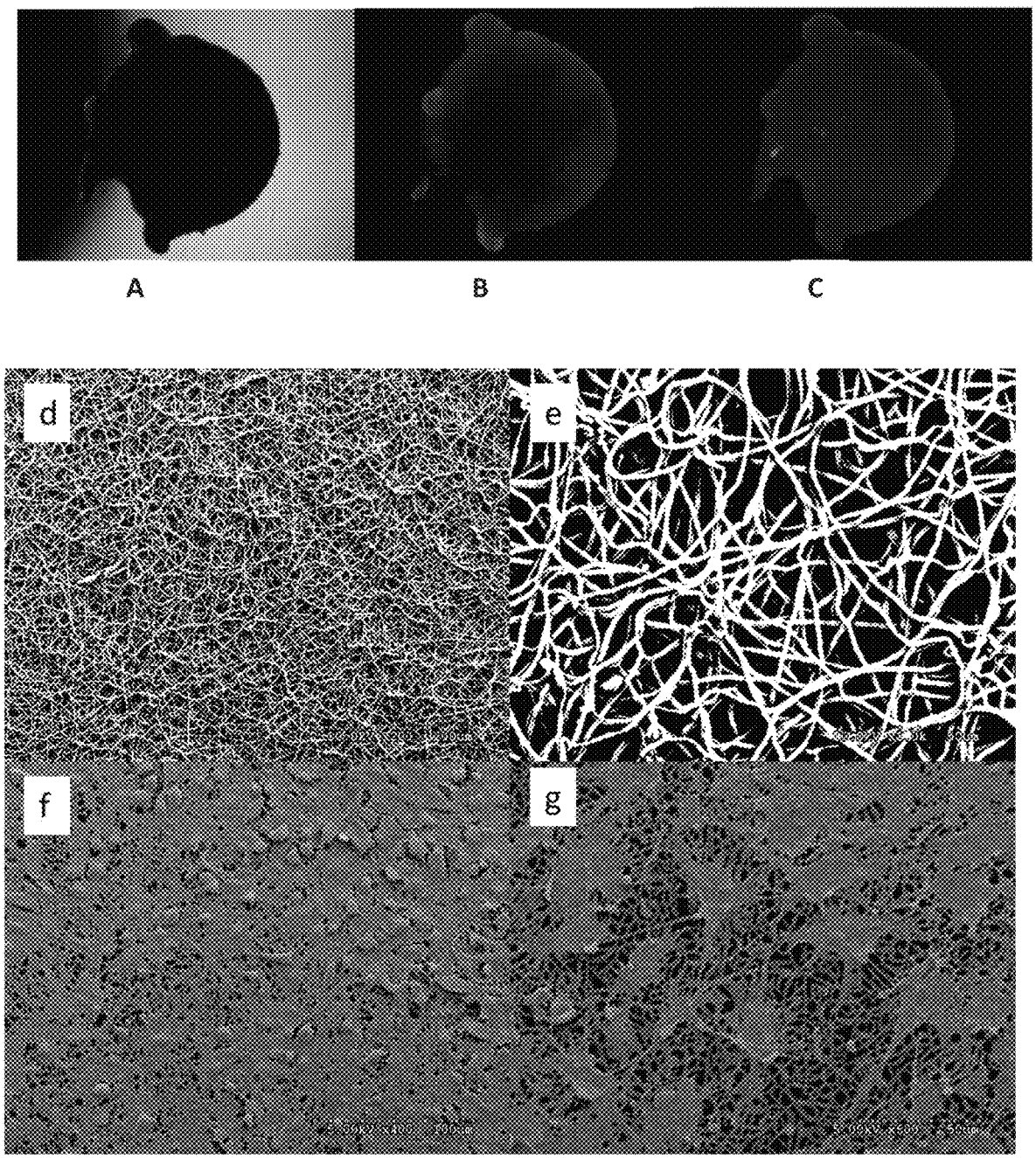
FIG. 9 shows images of 150 micron thick, random nanofiber mat cylinders with photoimmobilized PDL, populated with hippocampal cultures; Brightfield (A); fluorescent/calcein (B), fluorescent/Retrobeads® neuronal tracers (C), at 25× magnification.

In this example, small 3-dimensional nanofiber scaffold cylinders were generated, which were modified with PDL and pre-seeded with hippocampal cultures prior to their placement on a larger bioartificial tissue scaffold that contained multiple architectural elements. In this manner, for example, co-cultures were initiated on larger tissue scaffolds at desired locations, and in desired shapes and configurations, using the pre-seeded cell culture scaffolds (see Example 9). Photoreactive nanofiber cylinders shown in FIG. 9 (also seen in FIG. 10) were prepared and processed with PDL as described in Example 6, followed by further processing into 2 mm and 3 mm diameter cylinders using a circular die cutter. The small disc-shaped cylinders (150 microns thick) were seeded with hippocampal cultures as follows: the discs were seeded with a suspension of dissociated rat hippocampi (P0-4 SD rats, 300,000 cells/well, 24 well plate). After 3 hours, the discs were flipped upside down in fresh wells and re-seeded as before. After an additional 3 hours, the media was exchanged to remove the remaining suspension cells. NUNC Low-Cell-Binding plates (Thermo Fisher Scientific) were used to prevent cells from attaching to the wells. The 3D cell culture discs were monitored for 12 weeks using Brightfield and fluorescence microscopy. Cultures were otherwise maintained as described in Examples 6 and 7.

Results demonstrated that cells populated the scaffold cylinders and remained healthy for at least 12 weeks in culture as indicated by Calcein (Invitrogen) staining, as shown in FIG. 9b. In FIG. 9c, neurons are co-labeled with fluorescent Retrobeads® (LumaFluor, Inc.), which are nanoparticulate neural tract-tracers known to label neurons but not glia. Shown in FIGS. 9d and 9e are SEM images of the processed nanofiber cylinders. FIGS. 9f and 9g show hippocampal cultures (14 d.i.v.) growing on and penetrating the processed nanofiber cylinders.

Example 9

Lamination of Architectural Components to Generate a Bioartificial Hippocampal Brain Slice Tissue Scaffold Random and aligned nanofiber mats, prepared as described in the preceding examples, were used to generate laminated scaffolds supporting two populations of neuronal/glial mixed cultures. Although not required, a frame assembly was included to add tension, mechanical stability, and enhanced ease of handling to the scaffold. Aligned photoreactive nanofibers were used to guide neurite extension, axons, and dendrites between cell populations in a co-culture scaffold. An extracellular tissue architecture, modeled after the hippocampal Schaffer-collateral synapse to generate open field potentials, was provided by the assembled tissue scaffold and its components.

A 4×8 mm (ID) acetal frame was cut from acetal film using a digital die cutter. Markings (triangular notches and rectangular forceps handle, FIG. 10A) were included to denote the axial planes of the aligned fibers in the laminated assembly. The acetal frame was then coated in a coating solution containing 5% PCL (150 kD), in TFE, plus 0.5% Photoreactive Crosslinker by dipping, to facilitate subsequent annealing of PCL nanofiber mats to the frame. After drying, the coated frame was annealed to processed PDL-conjugated photoreactive nanofiber nonwoven mats and aligned fibers prepared as described in Example 6 (FIG. 7B) using a warm silver wire (heated to approximately 80° C. by shorting the silver wire across a 1.5 volt AA battery). Aligned photoreactive nanofibers were processed with PDL as in Example 6, except that the nanofibers were processed with PDL while suspended on the Secasanu-type collector plate. Ribbons of the processed aligned nanofibers were then collected directly onto the random nanofiber mats situated on top of the acetal frame assembly. The ribbons were collected perpendicular to each other using the frame notches as a guide, as indicated in FIG. 10A. The aligned nanofibers were then annealed to the assembly at their ends using a heated silver wire as described above. The aligned nanofiber ribbons and their perpendicular intersection can be seen in the Brightfield image in FIG. 10B.

Scaffold cylinders, prepopulated with hippocampal cultures as described in Example 8 (1 d.i.v.), were then placed on top of the scaffold assembly in culture as indicated by the black ovals in FIG. 10A. The level of culture media in the wells (24 well Nunc Low-Cell-Bind plate) was adjusted to create a liquid-air interface at the top of the cylinders on the scaffold assembly. The nanofiber cylinders spontaneously adhered to the laminated scaffold assembly after 24-28 hours, presumably due to cell migration, glial proliferation, and in situ production of extracellular matrix. The volume of culture media was then increased in the well. The seeded scaffold assemblies were then maintained in culture for up to 12 weeks.

Cells grew on the scaffolds and remained healthy for at least 12 weeks as indicated by Calcein (Invitrogen) staining, as shown in FIG. 10C. In FIG. 10D, neurons are co-labeled with fluorescent Retrobeads® (LumaFluor, Inc.), which are nanoparticulate neural tract-tracers known to label neurons but not glia. FIGS. 10C and 10D show the tissue comprises healthy live cells and indicates that the co-cultured neuronal populations appear to have innervated each other according to the scaffold architecture provided. Note that the Retro-Bead® fluorescence, which labels only neurons, indicates that axons followed the aligned nanofiber ribbons, but neuronal soma were infrequently seen on the aligned nanofiber ribbons. This was consistent with the two cell populations innervating each other along the aligned nanofiber tracts and remaining primarily embedded in their original locations, as provided by the scaffold architecture. Glial proliferation and migration was suggested by the calcein staining, as expected.

Example 10 fEPSP-Generating Bioartificial Tissues Induced by Scaffolds Containing Open-Field Architecture Dissociated hippocampal cells were seeded on open-field scaffolds and grown in an incubator as described in Example 9, to generate bioartificial open field hippocampal brain tissue "slices." FIG. 11 is a photo micrograph of the bioartificial tissue, on its scaffold, in a conventional field recording chamber. This type of field-recording setup is commonly used to capture evoked field responses from brain tissue slices that naturally possess open field architectures, such as hippocampus.

Bioartificial tissue scaffolds were removed from the incubator for electrophysiological testing between 14-90 days in vitro (d.i.v.). For electrophysiological field recordings, bioartificial tissue scaffolds were suspended on a nylon mesh in a small (350-400 µl) recording chamber (FIG. 11) and perfused with artificial cerebrospinal fluid (ACSF) at a rate of 2.5-3 ml/min (submerged mode). The temperature in the recording chamber was held at 30-32° C. Recordings were made using an ACSF-filled glass micropipette (2-4 MΩ) positioned as shown (FIG. 6) and connected via a head stage to the amplifier (A-M Systems model 1800). Signals were digitized at 100 kHz using a Digidata 1550 series interface (Axon instruments) running ClampEx 10.4. Synaptic responses were evoked by electrical stimulation using a bipolar tungsten electrode (tip spacing, 140 micrometers; Frederick Haer Company) and a 100 microsecond square wave test pulse was delivered at intervals of twenty seconds (FIG. 6). Stimulus-response relationship was established over the range of 0-1000 microV. The stimulation intensity was then adjusted to produce a basal response that was 25-30% of the maximum field EPSP amplitude.

Figure 12:
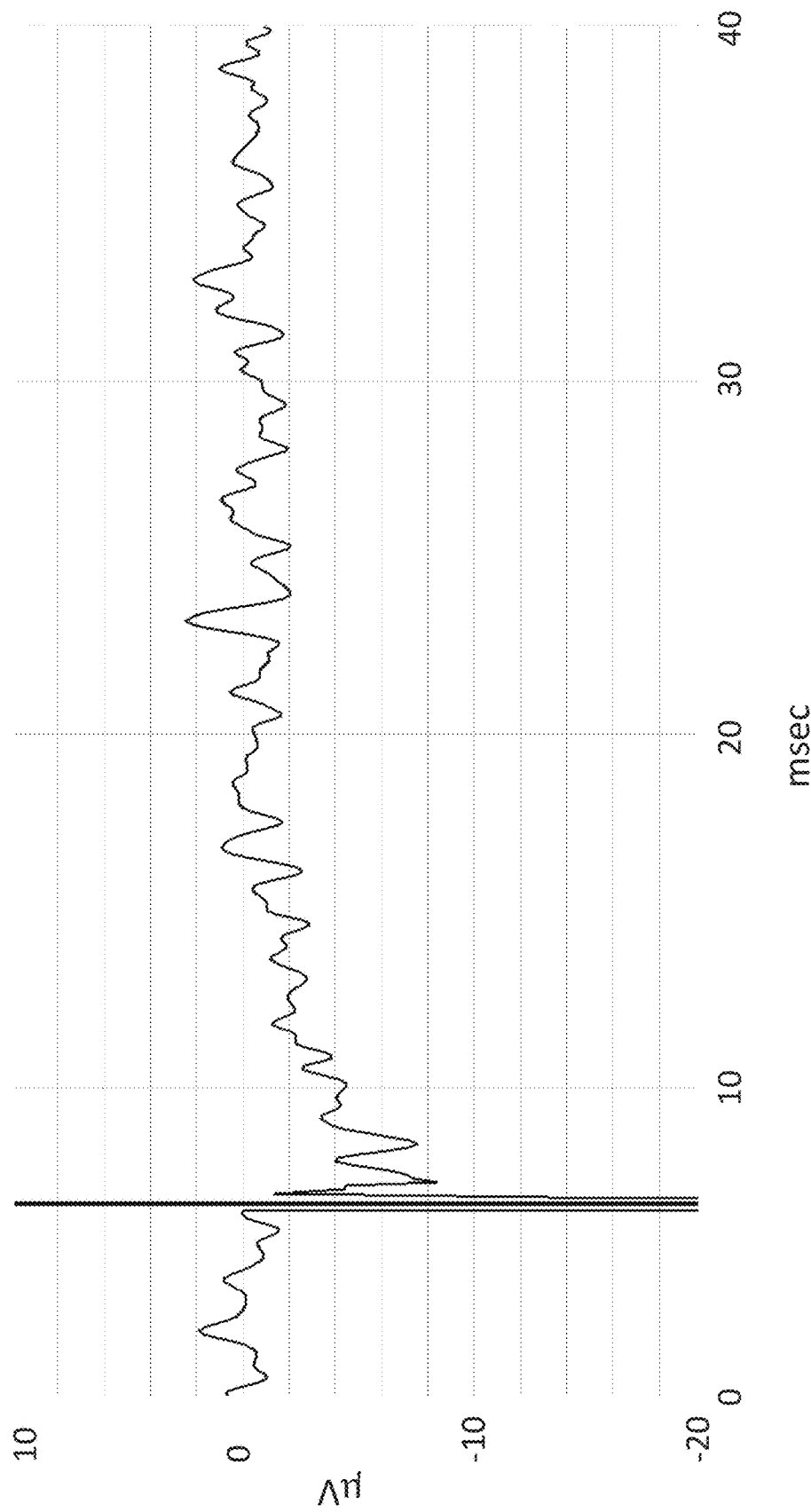
FIG. 12 is a graph showing the field fEPSP generated by the bioartificial tissue on the scaffold in response to orthodromic stimulation. The vertical line is the stimulus artifact.

FIG. 12 shows the field EPSP generated by the bioartificial brain tissue in response to orthodromic stimulation. The ability to generate an open field potential from dissociated rat hippocampi results from the growth patterning imparted by the scaffold to the bioartificial tissue during its morphogenesis in cell culture. Data in FIG. 12 shows the fEPSP response of a 28 d.i.v. bioartificial tissue scaffold seeded with P3 dissociated rat hippocampus. The cultures were not treated with ARA-C and therefore glia were proliferative. Because hippocampal synapses are primarily glutamatergic and gabaergic, the antagonists CNQX (AMPAR), APV (NMDAR) and Bicuculline (GABAR) were used to verify the pharmacological similarity of bioartificial hippocampal brain "slices" to natural hippocampal brain slices (acute brain slices) harvested from rats. Sixty evoked responses were collected using a stimulus intensity of 100 microA at $\frac{1}{20}$ Hz. After establishment of this basal synaptic field response, perfusion of the bioartificial tissue scaffold was changed from ACSF to ACSF plus CNQX (10 microM), APV (50 microM), and Bicuculline Methbromide (50 microM) to block ionotropic AMPA, NMDA, and GABA receptors, respectively. After a 10 minute drug wash-in period, an additional 60 evoked responses were collected and averaged. The averaged fEPSPs of the drug responses were collected in the presence of the drug cocktail and averaged. The averaged evoked fEPSP of the drug-treated tissue was then subtracted from the averaged evoked fEPSPs of the tissue prior to drug treatment, to control for potential artifacts and demonstrate sensitivity of the bioartificial rat hippocampal brain slice to standard excitatory and inhibitory neurotransmitter receptor antagonists. FIG. 12 shows the drug-subtracted average fEPSP. Neurochemicals were purchased from Sigma Aldrich.

In summary, this result demonstrated the ability of a bioartificial tissue scaffold containing an open field architecture to support the ontogeny of an in vivo like excitatory synaptic circuit. The circuit reflected the underlying open field architecture of the scaffold and was therefore capable of generating fEPSPs for extracellular field recording assays. Such bioartificial brain "slices," particularly when populated with human neurons derived from precursor cells, can be instrumental for drug development assays.

We claim:

1. A method of producing an electrophysiological assay scaffold comprising steps of:
   (a) providing a nanofibrous scaffold composed of unaligned polymeric nanofibers that form a nanofiber support having a planar surface;
   (b) printing, spraying, or brushing a cell culture agent at two or more physically isolated domains on the planar surface, thereby forming at least a first cell seeding domain and a second cell seeding domain, wherein the cell culture agent is present only at the cell seeding domains;
   (c) laminating the nanofiber support with a first planar-aligned nanofiber assembly and a second planar-aligned nanofiber assembly by placing the first planar-aligned nanofiber assembly at a location on the planar surface such that the first planar-aligned nanofiber assembly contacts the first cell seeding domain and does not contact the second cell seeding domain, and placing the second planar-aligned nanofiber assembly at a location on the planar surface such that the second planar-aligned nanofiber assembly contacts the second cell seeding domain, does not contact the first cell seeding domain, and contacts the first planar-aligned nanofiber assembly at an intersection that is located separate from the cell seeding domains, thereby forming a laminated scaffold;
   (d) annealing the first planar-aligned nanofiber assembly and second planar-aligned nanofiber assembly to the planar surface; and
   (e) culturing neurons on the distinct cell seeding domains under conditions to form functional chemical synapses between the neurons of the distinct cell seeding domains.

2. The method of claim 1 wherein step (c) comprises laminating the nanofiber support with nanofiber mats that comprise planar-aligned nanofibers.

3. The method of claim 1 wherein step (c) comprises laminating planar-aligned nanofiber assemblies comprising cell-adherent material.

4. The method of claim 3 wherein the cell-adherent material comprises ail extracellular matrix component, protein, cell attachment polymer, or a combination of any two or more of these.

5. The method of claim 4 wherein the cell-adherent material comprises poly-D-lysine.

6. The method of claim 1 wherein step (c) comprises laminating planar-aligned nanofiber assemblies composed of nanofibers comprising at least one chemically reactive functional group or latent reactive group.

7. The method of claim 6, wherein the latent reactive group comprises anthraquinone, aryl azide, aryl ketone, aryl ketone derivative, halophenyl azide, diazerine, or any mixtures or combinations of any of these.

8. The method of claim 7 further comprising a step of exposing the planar-aligned nanofiber assemblies to UV light.

9. The method of claim 6 wherein the chemically reactive group comprises an amine group.

10. The method of claim 1 wherein step (a) comprises providing a nanofibrous scaffold composed of randomly aligned polymeric nanofibers.

11. The method of claim 1 wherein step (a) comprises providing a nanofibrous scaffold having a pore size greater than 5 microns.

12. The method of claim 1 wherein step (a) comprises providing a nanofibrous scaffold composed of nanofibers comprising at least one chemically reactive functional group or latent reactive group.

13. The method of claim 12, wherein the latent reactive group comprises anthraquinone, aryl azide, aryl ketone, aryl ketone derivative, halophenyl azide, diazerine, or any mixtures or combinations of any of these.

14. The method of claim 13 further comprising a step of exposing the nanofibrous scaffold to UV light.

15. The method of claim 12 wherein the chemically reactive group comprises an amine group.

16. The method of claim 1 wherein step (b) comprises printing, spraying, or brushing a cell culture agent selected from extracellular matrix components, protein, cell attachment polymers, biological molecules that stimulate growth of nerve cells, or a combination of any two or more of these.

17. The method of claim 1 wherein step (d) comprises annealing the first planar-aligned nanofiber assembly and second planar-aligned nanofiber assembly to the planar surface using heat.

18. The method of claim 1 further comprising a step of providing a passivating polymer to an area of the scaffold outside the cell seeding domains.

19. The method of claim 18 wherein the step of providing passivating polymer to an area of the scaffold comprises applying the passivating polymer to the surface in combination with photolithographic masks or by printing.

* * * * *